United States Patent
McKinnon et al.

(10) Patent No.: US 11,090,120 B2
(45) Date of Patent: *Aug. 17, 2021

(54) SYSTEMS AND METHODS FOR OPTIMIZING PARAMETERS OF ORTHOPAEDIC PROCEDURES

(71) Applicant: Smith & Nephew, Inc., Memphis, TN (US)

(72) Inventors: Brian W. McKinnon, Arlington, TN (US); Ruxandra Cristiana Marinescu Tanasoca, Memphis, TN (US); Randy C. Winebarger, Southaven, MS (US); William L. Bowers, Jr., Southaven, MS (US); James Bennett Wiebe, III, Coldwater, MS (US); Nathaniel Milton Lenz, Germantown, TN (US); Zachary Christopher Wilkinson, Germantown, TN (US); Sean M. Haddock, Germantown, TN (US); Ryan Lloyd Landon, Southaven, MS (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/101,160

(22) Filed: Aug. 10, 2018

(65) Prior Publication Data
US 2018/0344407 A1    Dec. 6, 2018

Related U.S. Application Data

(63) Continuation of application No. 13/814,531, filed as application No. PCT/US2011/047775 on Aug. 15, 2011, now Pat. No. 10,064,686.
(Continued)

(51) Int. Cl.
*A61B 34/10* (2016.01)
*A61F 2/46* (2006.01)
(Continued)

(52) U.S. Cl.
CPC ............. *A61B 34/10* (2016.02); *A61F 2/46* (2013.01); *G09B 23/28* (2013.01); *A61B 5/107* (2013.01);
(Continued)

(58) Field of Classification Search
CPC ......... A61B 19/50; A61B 34/10; A61B 5/107; A61B 2034/102; A61B 2034/108;
(Continued)

(56) References Cited

U.S. PATENT DOCUMENTS

| 5,280,792 A | 1/1994 | Leong |
| 6,161,080 A | 12/2000 | Aouni-Ateshian et al. |

(Continued)

FOREIGN PATENT DOCUMENTS

| CN | 1757035 A | 4/2006 |
| CN | 101241601 A | 8/2008 |

(Continued)

OTHER PUBLICATIONS

Inkpen, "Precision and Accuracy in Computer Assisted Total Knee Replacement," Master's Degree Thesis, Department of Mechanical Engineering, University of British Columbia, 1999, 165 pages.*
(Continued)

*Primary Examiner* — Eunhee Kim
(74) *Attorney, Agent, or Firm* — Troutman Pepper Hamilton Sanders LLP

(57) ABSTRACT

Systems and methods for optimizing parameters of an orthopaedic procedure for a particular patient, including parameters relating to the anatomic and biomechanic fit of an implant or implant system implanted into the patient's
(Continued)

joint. These systems and methods may utilize patient-specific information gathered pre-operatively in conjunction with optimization algorithms to determine an optimal implant design and an optimal position and orientation for implantation of the implant into the particular patient's joint.

30 Claims, 15 Drawing Sheets

Related U.S. Application Data

(60) Provisional application No. 61/511,713, filed on Jul. 26, 2011, provisional application No. 61/509,928, filed on Jul. 20, 2011, provisional application No. 61/482,843, filed on May 5, 2011, provisional application No. 61/373,646, filed on Aug. 13, 2010.

(51) Int. Cl.
| | |
|---|---|
| *G09B 23/28* | (2006.01) |
| *A61B 5/107* | (2006.01) |
| *A61F 2/38* | (2006.01) |
| *A61F 2/44* | (2006.01) |
| *A61F 2/30* | (2006.01) |
| *G06F 30/00* | (2020.01) |

(52) U.S. Cl.
CPC ... *A61B 2034/102* (2016.02); *A61B 2034/108* (2016.02); *A61F 2/38* (2013.01); *A61F 2/44* (2013.01); *A61F 2002/30616* (2013.01); *A61F 2002/4633* (2013.01); *G06F 30/00* (2020.01)

(58) Field of Classification Search
CPC ...... A61F 2/46; A61F 2/38; A61F 2/44; A61F 2002/4633; A61F 2002/30616; G09B 23/28; G06F 17/50; G06F 30/00; A61L 334/10
USPC .......................................................... 703/1
See application file for complete search history.

(56) References Cited

U.S. PATENT DOCUMENTS

| | | | |
|---|---|---|---|
| 8,021,368 | B2 | 9/2011 | Haines |
| 8,062,302 | B2 | 11/2011 | Lang et al. |
| 2003/0153978 | A1 | 8/2003 | Whiteside |
| 2005/0119661 | A1 | 6/2005 | Hodgson et al. |
| 2007/0185498 | A2 | 8/2007 | Lavallee |
| 2007/0233267 | A1 | 10/2007 | Amirouche et al. |
| 2007/0255288 | A1 | 11/2007 | Mahfouz et al. |
| 2008/0281426 | A1 | 11/2008 | Fitz et al. |
| 2008/0319448 | A1* | 12/2008 | Lavallee ............... G06F 17/50 606/102 |
| 2009/0043556 | A1* | 2/2009 | Axelson ................ G06F 17/50 703/11 |
| 2009/0056299 | A1 | 3/2009 | Billado, Jr. et al. |
| 2009/0105834 | A1 | 4/2009 | Hovda et al. |
| 2009/0125117 | A1 | 5/2009 | Paradis et al. |
| 2009/0204222 | A1 | 8/2009 | Burstein et al. |
| 2009/0264894 | A1* | 10/2009 | Wasielewski ........ A61B 34/10 606/102 |
| 2009/0265012 | A1 | 10/2009 | Engh et al. |
| 2010/0007656 | A1 | 1/2010 | Otto et al. |
| 2010/0049195 | A1* | 2/2010 | Park .................. A61B 17/1764 606/87 |
| 2010/0076563 | A1* | 3/2010 | Otto .................... A61B 5/4824 623/20.14 |
| 2010/0086181 | A1 | 4/2010 | Zug et al. |
| 2010/0106475 | A1 | 4/2010 | Smith et al. |
| 2011/0029093 | A1* | 2/2011 | Bojarski ................ A61F 2/389 623/20.35 |
| 2011/0112808 | A1 | 5/2011 | Anderson et al. |
| 2011/0212090 | A1 | 9/2011 | Pedersen et al. |

FOREIGN PATENT DOCUMENTS

| | | |
|---|---|---|
| EP | 0611160 A2 | 8/1994 |
| EP | 1413264 A2 | 4/2004 |
| JP | 2009501036 A | 1/2009 |
| JP | 2009056299 A | 3/2009 |
| JP | 2014521835 A | 8/2014 |
| WO | 2007009719 A1 | 1/2007 |
| WO | 2009106816 A1 | 9/2009 |

OTHER PUBLICATIONS

Haruna, et al., "Clinical Medical Engineering Upskilling Lectures", First Edition, Osaka University Press, Seiichi Washida, Mar. 19, 2010, pp. 173-174.

Illsley, et al., "IntraoperativelyMeasuring Ligamentous Constraint and Determining Optimal Component Placement During Computer Assisted Total Knee Replacment", Master's Degree Thesis, Department of Mechanical Engineering, University of New Brunswick, 1999, 136 pages.

Inkpen, et al., "Precision and Accuracy in Computer Assisted Total Knee Replacement", Master's Degree Thesis, Department of Mechanical Engineering, University of British Columbia, 1999, 165 pages.

Kutzner, et al., " Loading of the Knee Joint During Activities of Daily Living Measured In Vivo in Five Subjects" Journal of Biomechanics, vol. 43, 2010, pp. 2164-2173.

Taylor, et al., "Tibio Femoral Loading During Human Gait and Stair Climbing," Journal of Orthopaedic Research, vol. 22, No. 3, May 1, 2004, pp. 625-632.

Chinese Third Office Action, Chinese Patent Office, Chinese Patent Application No. 2017109698493, dated Jan. 20, 2020, 9 pages.

India Office Action for 1344/DELNP/2013 dated Dec. 9, 2019.

* cited by examiner $$R_1 = A*F_1 + B*F_2 + C*F_3 +...+ X*F_n$$
$$R_2 = D*F_1 + E*F_3 +...+ Y*F_n$$
$$R_3 = Q*F_2 + R*F_3 +...+ Z*F_n$$
$$...$$
$$R_n = ...$$
FIG. 11
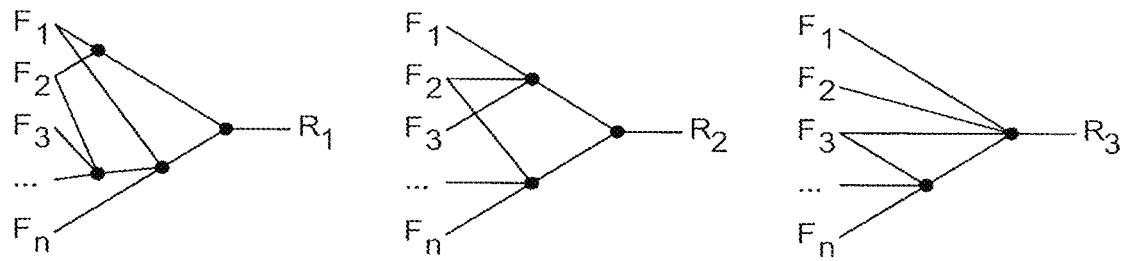
FIG. 12
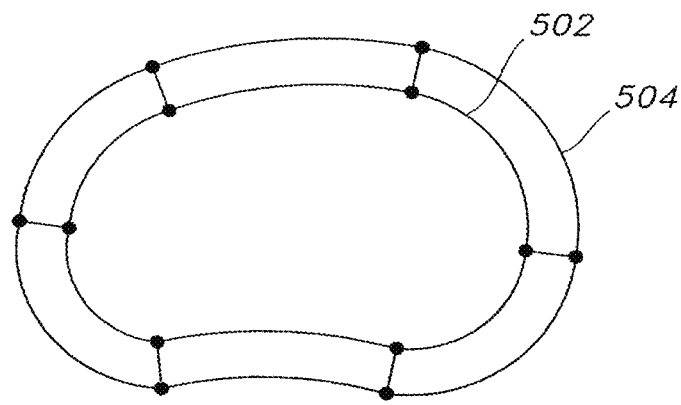
FIG. 13

SYSTEMS AND METHODS FOR OPTIMIZING PARAMETERS OF ORTHOPAEDIC PROCEDURES

RELATED APPLICATIONS

This patent application is a continuation application of U.S. patent application Ser. No. 13/814,648, now U.S. Pat. No. 10,631,932, filed on May 13, 2013, and titled "Systems and Methods for Optimizing Parameters of Orthopaedic Procedures," which is a U.S. National Stage filing under 35 U.S.C. § 371 of International Application No. PCT/US2011/47784 filed Aug. 15, 2011 entitled Systems and Methods for Optimizing Parameters of Orthopaedic Procedures," which claims the benefit the filing date of U.S. provisional application Ser. No. 61/373,646, filed Aug. 13, 2010 for a "Method of Developing a Patient-Matched Algorithm for Knee Design," 61/482,843, filed May 5, 2011 for "Optimization Systems and Methods for Orthopaedic Systems," 61/509,928, filed Jul. 20, 2011 for "Systems and Methods for Optimizing Fit of an Implant to Anatomy," and 61/511,713, filed Jul. 26, 2011 for "Systems and Methods for Optimizing Fit of an Implant to Anatomy," the entire contents of each of which are hereby incorporated by reference into this patent application.

RELATED FIELDS

Systems and methods for optimizing parameters of orthopaedic procedures, such as systems and methods for optimizing the biomechanic and anatomic fit of an orthopaedic implant into a particular patient's joint.

BACKGROUND

Simple joints such as the ball and socket joint (e.g. hip and shoulder), the pivot joint (e.g. elbow) or more complex joints such as the condylar joint (e.g. knee joint) are incredibly intricate systems, whose performance can be significantly affected by various factors. Procedures for replacing, resurfacing, or otherwise repairing these joints are common, such as in response to damage or other degradation of the joint. For instance, total knee arthroplasty, which replaces the articular surfaces of the femur, tibia and patella with artificial implants, is a common procedure for patients suffering from degradation or trauma to the knee joint. Given the complexities of systems such as knee joints, however, it is difficult to identify implant geometries and a position and orientation for implantation using current technologies that will produce optimal joint function in a particular patient. Furthermore, many implant systems currently available only provide a limited number of size options, making it even more difficult to optimize an orthopaedic procedure for a particular patient.

SUMMARY

Embodiments of the present invention are directed to systems and methods for optimizing parameters of an orthopaedic procedure for a particular patient, including parameters relating to the anatomic fit (e.g. implant coverage of resections, strength of interface between an implant and the anatomy, degree of resection (i.e. how much or little bone is removed)) and biomechanic fit (e.g. joint kinematics, kinetics, and/or ligament (or other soft tissue) balance) of an implant implanted into the patient's joint. These systems and methods may utilize patient-specific information gathered pre-operatively in conjunction with optimization algorithms to determine an optimal implant design and an optimal size, position and orientation for implantation of the implant into the particular patient's joint. In some embodiments, the implant design is chosen from a hierarchy of pre-designed orthopaedic implants in which each implant reflects a general size group option, an anatomic size option, and a biomechanic size option, the anatomic and biomechanic size options being, at least in some embodiments, sets of different and at least somewhat independent features of the orthopaedic implant design. In some embodiments, at least one of the optimization algorithms utilizes a defined relationship between several orthopaedic factors and orthopaedic responses in order to determine optimal parameters for the orthopaedic procedure to achieve desired orthopaedic responses. In some embodiments, optimization systems and methods may be used to optimize parameters of an orthopaedic procedure other than or in addition to anatomic and biomechanic fit of an implant for the particular patient. For instance, in some embodiments, these systems and methods may be utilized to optimize other aspects of a patient's treatment such as selection of and optimization of additional treatments, such as custom orthotics or rehabilitation regimens.

In some embodiments, there may be provided a computer-implemented method of optimizing parameters relating to a joint procedure involving the implantation of at least one orthopaedic implant into a joint of a particular patient, the method comprising: receiving in a computer processor information concerning the particular patient, including: (i) information relating at least in part to a model of the particular patient's joint, including information defining at least in part a plurality of soft tissue attachment locations; (ii) information relating at least in part to an axis associated with the particular patient's joint in relation to the model of the particular patient's joint; receiving in the computer processor information that defines at least one relationship relating a plurality of orthopaedic responses to a plurality of orthopaedic factors, wherein: (i) at least some of the plurality of orthopaedic responses each relate to at least one of a kinetic, kinematic, and soft tissue balance response of the joint; (ii) at least some of the orthopaedic factors relate to the received information concerning the particular patient; (iii) at least one of the orthopaedic factors relates to at least one of a position and an orientation of the orthopaedic implant relative to the joint; and (iv) at least one of the orthopaedic factors relates to an articular surface shape geometry of the orthopaedic implant; in the computer processor, using the received information concerning the particular patient, and using the received information that defines the at least one relationship, automatically determining: (i) at least one of a suggested optimal position and a suggested optimal orientation for the orthopaedic implant relative to the particular patient's joint; and (ii) a suggested optimal articular surface shape geometry for the orthopaedic implant; outputting from the computer processor information concerning the at least one of the suggested optimal position and orientation for the orthopaedic implant and information concerning the suggested optimal articular surface shape geometry for the orthopaedic implant.

In some embodiments, there may be provided a method in which receiving information relating at least in part to the model of the particular patient's joint comprises receiving information relating at least in part to at least one articular surface of the particular patient's joint.

In some embodiments, there may be provided a method in which receiving information relating at least in part to the model of the particular patient's joint comprises receiving information relating at least in part to a three-dimensional model of the particular patient's joint.

In some embodiments, there may be provided a method in which receiving information relating at least in part to a three-dimensional model of the particular patient's joint includes receiving information defining a medial condylar articular surface, a lateral condylar articular surface, and a patello-femoral articular surface; and receiving information relating at least in part to an axis associated with the particular patient's joint includes receiving information defining a mechanical axis of a leg relative to the three-dimensional model of the particular patient's joint.

In some embodiments, there may be provided a method in which receiving information relating at least in part to a three-dimensional model of the particular patient's joint includes receiving information defining at least one of tibial articular surface and a patellar articular surface.

In some embodiments, there may be provided a method in which receiving information concerning the particular patient further comprises receiving information relating to at least one of: a gait of the particular patient; an anthropometric characterization of the particular patient; a lifestyle of the particular patient; at least one physiological attribute of the particular patient; an earlier injury of the particular patient; a co-morbidity condition of the particular patient, a demographic characterization of the particular patient, and a bone strength characterization of the particular patient.

In some embodiments, there may be provided a method in which determining the at least one suggested optimal position and optimal orientation and the suggested optimal articular surface shape geometry further comprises using uncertainty information relating to the information concerning the particular patient.

In some embodiments, there may be provided a method in which using the uncertainty information comprises using a probability distribution.

In some embodiments, there may be provided a method in which using the probability distribution comprises using a probability distribution relating at least in part to the information relating to the plurality of soft tissue attachment locations.

In some embodiments, there may be provided a method in which receiving in the computer processor information that defines the relationship relating the orthopaedic responses to the orthopaedic factors comprises receiving at least one of a plurality of equations, a plurality of trained neural networks, and a plurality of support vector machines.

In some embodiments, there may be provided a method in which receiving information that defines the relationship comprises receiving information defining the relationship such that at least some of the orthopaedic responses relate to one or more of range of motion, joint stability, joint strength and ligament balance.

In some embodiments, there may be provided a method in which receiving information that defines the relationship comprises receiving information defining the relationship such that at least one of the orthopaedic responses relate to overall balance of an orthopaedic system including a plurality of joints.

In some embodiments, there may be provided a method in which receiving the information defining the relationship relating the orthopaedic responses to the orthopaedic factors further comprises receiving information defining a weight for each of the orthopaedic responses, wherein at least some of the weights are different.

In some embodiments, there may be provided a method in which determining the suggested optimal articular shape geometry comprises determining a suggested optimal medial condylar articular shape geometry for a femoral implant, a suggested optimal lateral condylar articular shape geometry for the femoral implant, and a suggested optimal trochlear groove articular shape geometry for the femoral implant.

In some embodiments, there may be provided a method which further comprises determining, using the information relating to the three-dimensional model of the particular patient's joint and the suggested optimal position and the suggested optimal orientation for the orthopaedic implant relative to the particular patient's joint, suggested optimal size coverage geometry for the orthopaedic implant.

In some embodiments, there may be provided a method further comprising manufacturing the orthopaedic implant including the suggested optimal size coverage geometry and the suggested optimal articular surface shape geometry.

There may also be provided a system for optimizing parameters of a joint procedure involving the implantation of at least one orthopaedic implant into a joint of a particular patient, the system comprising: a processor; and a storage medium comprising a computer optimizer application that, when executed by the processor, is configured to cause the system to: (i) access information concerning the particular patient, including information relating at least in part to a model of the particular patient's joint, including information defining at least in part a plurality of soft tissue attachments, and information relating at least in part to an axis associated with the particular patient's joint in relation to the model of the particular patient's joint; (ii) access information that defines at least one relationship relating a plurality of orthopaedic responses to a plurality of orthopaedic factors, wherein: at least some of the plurality of orthopaedic responses each relate to at least one of a kinetic, kinematic, and soft tissue balance response of the joint; at least some of the orthopaedic factors relate to the accessed information concerning the particular patient; at least one of the orthopaedic factors relates to at least one of a position and an orientation of the orthopaedic implant relative to the joint; and at least one of the orthopaedic factors relates to an articular surface shape geometry of the orthopaedic implant; using the accessed information concerning the particular patient, and using the accessed information that defines the at least one relationship, automatically determining: at least one of a suggested optimal position and a suggested optimal orientation for the orthopaedic implant relative to the particular patient's joint; and a suggested optimal articular surface shape geometry for the orthopaedic implant; and outputting from the computer processor information concerning the at least one of the suggested optimal position and orientation for the orthopaedic implant and information concerning the suggested optimal articular surface shape geometry for the orthopaedic implant.

In some embodiments, there may be provided a system wherein accessing information relating at least in part to the model of the particular patient's joint comprises accessing information relating at least in part to at least one articular surface of the particular patient's joint.

In some embodiments, there may be provided a system wherein accessing information relating at least in part to the model of the particular patient's joint comprises accessing information relating at least in part to a three-dimensional model of the particular patient's joint.

In some embodiments, there may be provided a system wherein accessing information relating at least in part to a three-dimensional model of the particular patient's joint includes receiving information defining a medial condylar articular surface, a lateral condylar articular surface, and a patello-femoral articular surface; and accessing information relating at least in part to an axis associated with the particular patient's joint includes receiving information defining a mechanical axis of a leg relative to the three-dimensional model of the particular patient's joint.

In some embodiments, there may be provided a system wherein accessing information relating at least in part to a three-dimensional model of the particular patient's joint includes accessing information defining at least one of tibial articular surface and a patellar articular surface.

In some embodiments, there may be provided a system wherein accessing information concerning the particular patient further comprises accessing information relating to at least one of: a gait of the particular patient; an anthropometric characterization of the particular patient; a lifestyle of the particular patient; at least one physiological attribute of the particular patient; an earlier injury of the particular patient; a co-morbidity condition of the particular patient, a demographic characterization of the particular patient, and a bone strength characterization of the particular patient.

In some embodiments, there may be provided a system wherein determining the at least one suggested optimal position and optimal orientation and the suggested optimal articular surface shape geometry further comprises using uncertainty information relating to the information concerning the particular patient.

In some embodiments, there may be provided a system wherein using the uncertainty information comprises using a probability distribution.

In some embodiments, there may be provided a system wherein using the probability distribution comprises using a probability distribution relating at least in part to the information relating to the plurality of soft tissue attachment locations.

In some embodiments, there may be provided a system wherein accessing information that defines the relationship relating the orthopaedic responses to the orthopaedic factors comprises accessing at least one of a plurality of equations, a plurality of trained neural networks, and a plurality of support vector machines.

In some embodiments, there may be provided a system wherein accessing information that defines the relationship comprises accessing information defining the relationship such that at least some of the orthopaedic responses relate to one or more of range of motion, joint stability, joint strength and ligament balance.

In some embodiments, there may be provided a system wherein accessing information that defines the relationship comprises receiving information defining the relationship such that at least one of the orthopaedic responses relate to overall balance of an orthopaedic system including a plurality of joints.

In some embodiments, there may be provided a system wherein accessing the information defining the relationship relating the orthopaedic responses to the orthopaedic factors further comprises receiving information defining a weight for each of the orthopaedic responses, wherein at least some of the weights are different.

In some embodiments, there may be provided a system wherein determining the suggested optimal articular shape geometry comprises determining a suggested optimal medial condylar articular shape geometry for a femoral implant, a suggested optimal lateral condylar articular shape geometry for the femoral implant, and a suggested optimal trochlear groove articular shape geometry for the femoral implant.

In some embodiments, there may be provided a system wherein the computer optimizer algorithm is configured to cause the system to determine, using the information relating to the three-dimensional model of the particular patient's joint and the suggested optimal position and the suggested optimal orientation for the orthopaedic implant relative to the particular patient's joint, suggested optimal size coverage geometry for the orthopaedic implant.

There may also be provided a computer-implemented method of optimizing parameters of a joint procedure involving the implantation of at least one orthopaedic implant into a joint of a particular patient, the method comprising: receiving in a computer processor information concerning the particular patient, including information relating at least in part to a model of the particular patient's joint; in the computer processor, using the information relating to the model, determining a suggested optimal general size group for the orthopaedic implant; in the computer processor, using the information relating to the model and the information relating to the suggested optimal general size group, determining at least one of a suggested optimal position and a suggested optimal orientation for the orthopaedic implant relative to the particular patient's joint; in the computer processor, using the information relating to the model, the information relating to the suggested optimal general size group, and the information relating to the at least one of the suggested optimal position and the suggested optimal orientation, determining a suggested anatomic fit geometry for the orthopaedic implant; and outputting from the computer processor the information relating to the suggested optimal general size group and the information relating to suggested anatomic fit geometry.

In some embodiments, there may be provided a method wherein receiving the information relating at least in part to the model of the particular patient's joint comprises receiving information relating at least in part to a three-dimensional model of the particular patient's joint.

In some embodiments, there may be provided a method wherein determining the suggested optimal general size group for the orthopaedic implant comprises selecting the suggested optimal general size group from a plurality of possible general size group options based on at least one dimension of the three-dimensional model of the particular patient's joint.

In some embodiments, there may be provided a method wherein determining the suggested optimal general size group for the orthopaedic implant further comprises selecting the suggested optimal general size group based on at least one anterior-posterior or medial-lateral dimension of the three-dimensional model of the particular patient's joint.

In some embodiments, there may be provided a method wherein determining the suggested optimal position and suggested optimal orientation for the orthopaedic implant relative to the particular patient's joint further comprises determining a suggested articular surface shape geometry of the orthopaedic implant.

In some embodiments, there may be provided a method wherein determining the suggested articular surface shape geometry of the orthopaedic implant comprises determining a medial condylar articular surface shape geometry, a lateral condylar articular surface shape geometry, and a patello-femoral groove articular surface shape geometry of the orthopaedic implant.

In some embodiments, there may be provided a method wherein determining the suggested articular surface shape geometry of the orthopaedic implant comprises determining an articular surface shape geometry for at least one of a tibial implant and a patellar implant.

In some embodiments, there may be provided a method wherein determining the suggested articular surface shape geometry comprises selecting the suggested articular surface shape geometry from a plurality of possible articular surface shape geometry options.

In some embodiments, there may be provided a method wherein outputting the information comprises outputting information relating to a suggested orthopaedic implant from the suggested optimal general size group incorporating the suggested anatomic fit geometry and the suggested articular surface shape geometry.

In some embodiments, there may be provided a method wherein receiving in the computer processor information concerning the particular patient comprises receiving information relating at least in part to an axis associated with the particular patient's joint in relation to the three-dimensional model of the particular patient's joint, and receiving information relating at least in part to a plurality of soft tissue attachment locations in relation to the three-dimensional model of the particular patient's joint.

In some embodiments, there may be provided a method wherein determining at least one of the suggested optimal position and the suggested optimal orientation for the orthopaedic implant further comprises using the information relating to the axis and the soft tissue attachment locations to determine at least one of the suggested optimal position and the suggested optimal orientation.

In some embodiments, there may be provided a method wherein using the information relating to the soft tissue attachment locations further comprises using information relating to an uncertainty distribution.

In some embodiments, there may be provided a method wherein receiving in the computer processor information concerning the particular patient comprises receiving additional information relating at least in part to at least one of: a gait of the particular patient; an anthropometric characterization of the particular patient; a lifestyle of the particular patient; at least one physiological attribute of the particular patient; an earlier injury of the particular patient; and a co-morbidity condition of the particular patient.

In some embodiments, there may be provided a method wherein determining at least one of the suggested optimal position and the suggested optimal orientation for the orthopaedic implant further comprises using the additional information to determine at least one of the suggested optimal position and the suggested optimal orientation.

In some embodiments, there may be provided a method wherein outputting the information further comprises outputting information relating to a custom surgical instrument for facilitating the implantation of the orthopaedic implant into the particular patient.

In some embodiments, there may be provided a method wherein outputting the information relating to the custom surgical instrument further comprises outputting information relating to a surface on the custom surgical instrument having a shape based on the three-dimensional model of the particular patient's joint.

In some embodiments, there may be provided a method wherein determining the suggested anatomic fit geometry for the orthopaedic implant comprises determining a suggested perimeter geometry for the orthopaedic implant from a plurality of possible perimeter geometry options for the orthopaedic implant.

There may also be provided a system for optimizing parameters of a joint procedure involving the implantation of at least one orthopaedic implant into a joint of a particular patient, the system comprising: a processor; and a storage medium comprising a computer optimizer application that, when executed by the processor, is configured to cause the system to: (i)

access information concerning the particular patient, including information relating at least in part to a three-dimensional model of the particular patient's joint; (ii) use the information relating to the three-dimensional model to determine a suggested optimal general size group for the orthopaedic implant; (iii) use the information relating to the three-dimensional model and the information relating to the suggested optimal general size group to determine at least one of a suggested optimal position and a suggested optimal orientation for the orthopaedic implant relative to the particular patient's joint; (iv) use the information relating to the three-dimensional model, the information relating to the suggested optimal general size group, and the information relating to the at least one of the suggested optimal position and the suggested optimal orientation to determine a suggested anatomic fit geometry for the orthopaedic implant; and (v) output from the processor the information relating to the suggested optimal general size group and the information relating to suggested anatomic fit geometry.

In some embodiments, there may be provided a system wherein the computer optimizer application, when executed by the processor, is configured to cause the system to select the suggested optimal general size group from a plurality of possible general size groups based on at least one dimension of the three-dimensional model of the particular patient's joint.

In some embodiments, there may be provided a system wherein the computer optimizer application, when executed by the processor, is configured to cause the system to select the suggested optimal general size group based on at least one anterior-posterior or medial-lateral dimension of the three-dimensional model of the particular patient's joint.

In some embodiments, there may be provided a system wherein the computer optimizer application, when executed by the processor, is configured to cause the system to determine a suggested articular surface shape geometry of the orthopaedic implant.

In some embodiments, there may be provided a system wherein the computer optimizer application, when executed by the processor, is configured to cause the system to determine a medial condylar articular surface shape geometry, a lateral condylar articular surface shape geometry, and a patello-femoral groove articular surface shape geometry of the orthopaedic implant.

In some embodiments, there may be provided a system wherein the computer optimizer application, when executed by the processor, is configured to cause the system to select the suggested articular surface shape geometry from a plurality of possible articular surface shape geometries.

In some embodiments, there may be provided a system wherein the computer optimizer application, when executed by the processor, is configured to cause the system to output information relating to a suggested orthopaedic implant from the suggested optimal general size group incorporating the suggested anatomic fit geometry and the suggested articular surface shape geometry.

In some embodiments, there may be provided a system wherein the computer optimizer application, when executed by the processor, is configured to cause the system to access: information relating at least in part to an axis associated with the particular patient's joint in relation to the three-dimensional model of the particular patient's joint; and information relating at least in part to a plurality of soft tissue attachment locations in relation to the three-dimensional model of the particular patient's joint.

In some embodiments, there may be provided a system wherein the computer optimizer application, when executed by the processor, is configured to cause the system to use the information relating to the axis and the soft tissue attachment locations in determining at least one of the suggested optimal position and the suggested optimal orientation.

In some embodiments, there may be provided a system wherein the computer optimizer application, when executed by the processor, is configured to cause the system to use information relating to an uncertainty distribution of the soft tissue attachment locations in determining at least one of the suggested optimal position and the suggested optimal orientation.

In some embodiments, there may be provided a system wherein the computer optimizer application, when executed by the processor, is configured to cause the system to access additional information relating at least in part to at least one of: a gait of the particular patient; an anthropometric characterization of the particular patient; a lifestyle of the particular patient; at least one physiological attribute of the particular patient; an earlier injury of the particular patient; and a co-morbidity condition of the particular patient.

In some embodiments, there may be provided a system wherein the computer optimizer application, when executed by the processor, is configured to access uncertainty information concerning the particular patient.

In some embodiments, there may be provided a system wherein the computer optimizer application, when executed by the processor, is configured to use the additional information in determining at least one of the suggested optimal position and the suggested optimal orientation.

In some embodiments, there may be provided a system wherein the computer optimizer application, when executed by the processor, is configured to output information relating to a custom surgical instrument for installing the orthopaedic implant into the particular patient.

In some embodiments, there may be provided a system wherein the computer optimizer application, when executed by the processor, is configured to output information relating to a surface on the custom surgical instrument having a shape based on the three-dimensional model of the particular patient's joint.

In some embodiments, there may be provided a system wherein the computer optimizer application, when executed by the processor, is configured to determine the suggested anatomic fit geometry by determining a suggested perimeter geometry for the orthopaedic implant from a plurality of possible perimeter geometries for the orthopaedic implant.

BRIEF DESCRIPTION OF DRAWINGS

FIG. 11 schematically illustrates a set of mathematical equations used in one non-limiting example of a biomechanic fit optimization step.

FIG. 12 schematically illustrates a set of neural networks used in another example of a biomechanic fit optimization step.

FIG. 13 schematically illustrates one non-limiting example of a anatomic fit optimization step.

DETAILED DESCRIPTION

Figure 1A:
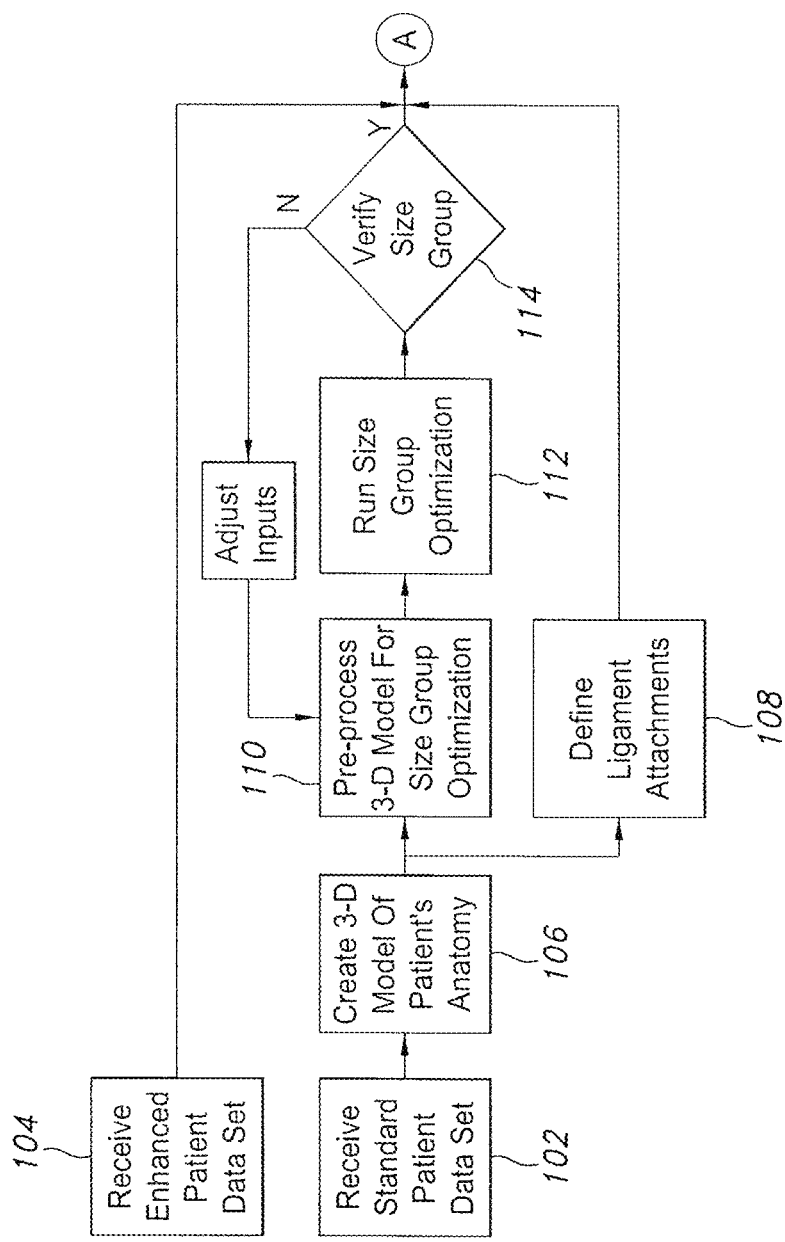
FIGS. 1a and b schematically illustrate one non-limiting example of a method for optimizing parameters of an orthopaedic procedure for a particular patient.
Figure 1B:
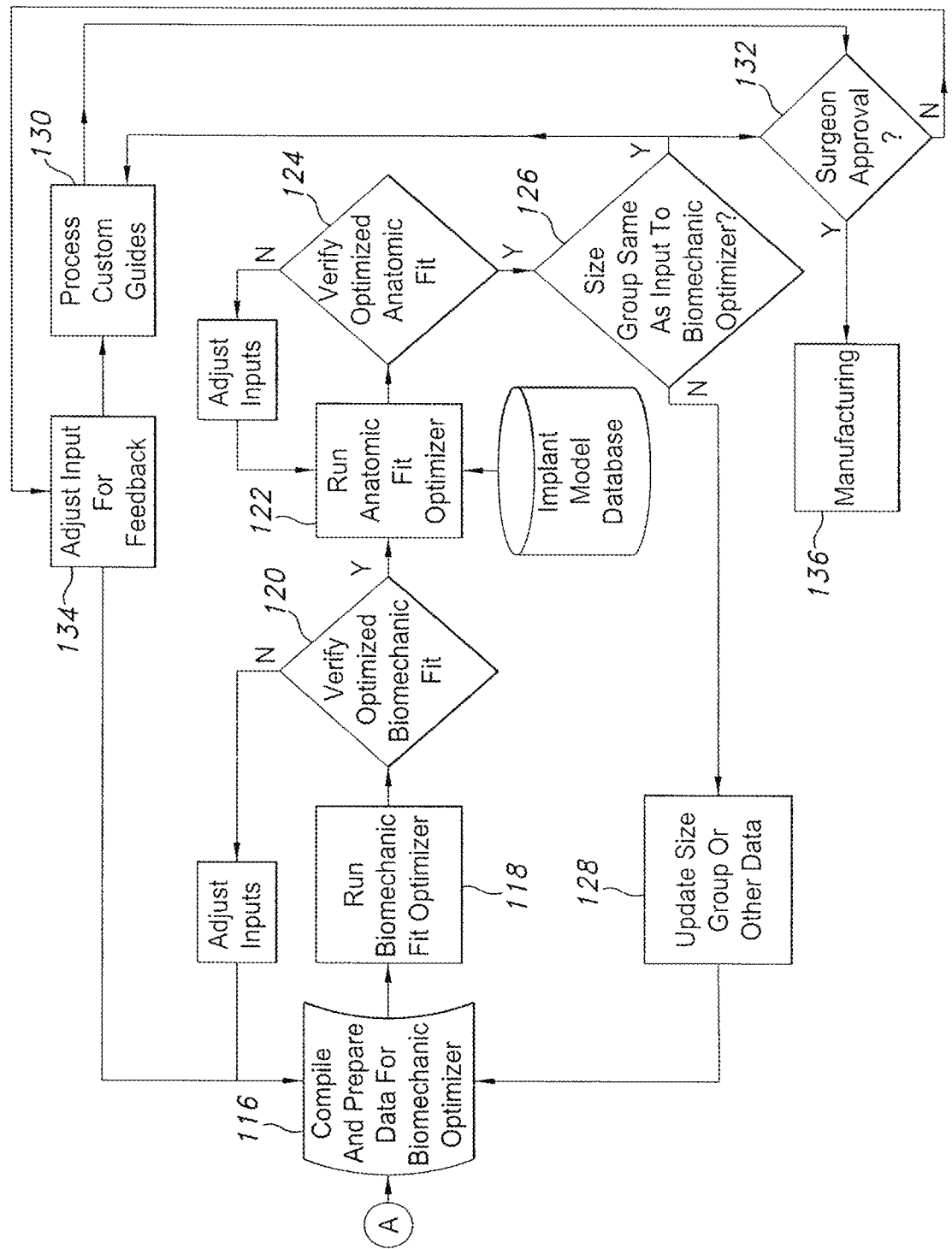
Figure 2:
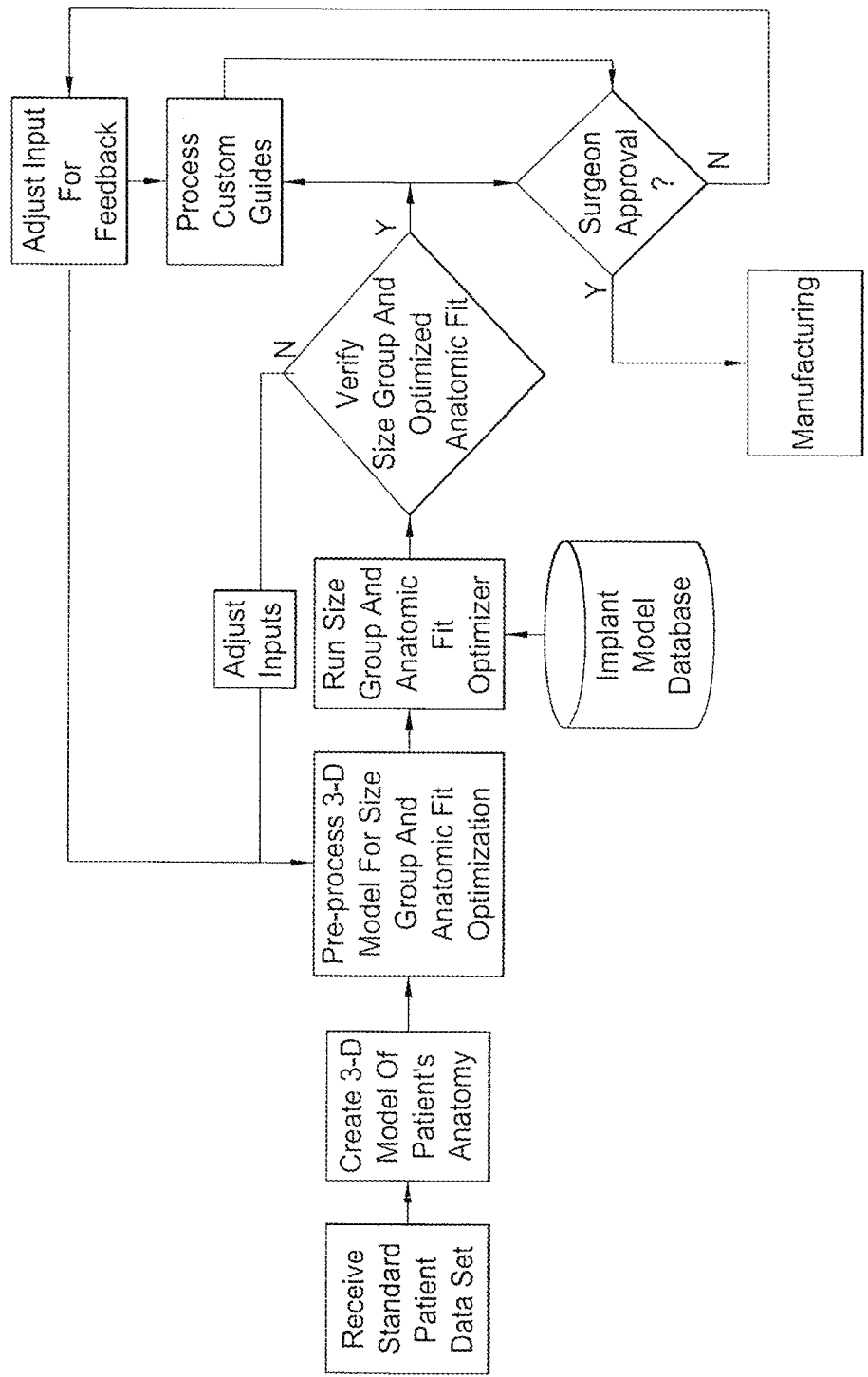
FIG. 2 schematically illustrates another example of a method for optimizing parameters of an orthopaedic procedure for a particular patient.

FIGS. 1 and 2 illustrate non-limiting examples of methods for optimizing parameters of an orthopaedic procedure. In these particular examples, the methods are directed to optimizing parameters for total knee arthroplasty procedures, although those of skill in the art will recognize that these or similar methods may be used for other types of orthopaedic procedures, such as other types of knee arthroplasty (e.g. uni-compartmental or bi-compartmental), hip arthroplasty, shoulder arthroplasty, joint resurfacing, or spinal procedures. The methods illustrated in FIGS. 1 and 2 may be used to optimize one or several parameters of an orthopaedic procedure. For instance, the method illustrated in FIGS. 1a and b facilitates optimization of anatomic fit and biomechanic fit of an orthopaedic implant to a particular patient whereas the method illustrated in FIG. 2 facilitates optimization of just an anatomic fit to a particular patient, not biomechanic fit.

FIGS. 1a and b—Optimized Anatomic and Biomechanic Fit

FIGS. 1a and b schematically illustrate one non-limiting example of a method for optimizing anatomic and biomechanic fit of an implant to a particular patient for a total knee arthroplasty procedure. In this example, the method identifies an optimal implant for the patient's particular anatomy and biomechanics as well as an optimal position and orientation (e.g. in six degrees of freedom) for implantation of the implant. In this example, these optimized parameters are output in the form of data reflecting a recommended femoral component, tibial component, and optionally patellar component, and custom cutting guides for implanting the components in the patient's joint. In other embodiments, the optimized parameters may be output or otherwise utilized in other forms and manners. For instance, outputs could include settings for non-custom cutting guides or systems (e.g. settings for a computer assisted navigation system or settings on an adjustable cutting guide).

In the embodiment of FIGS. 1a and b, the recommended femoral, tibial and patellar components are identified from a database or other collection of pre-designed femoral, tibial and patellar component options, which may be in the form of digital three dimensional CAD models of the femoral, tibial and patellar component options, or in other forms. In some embodiments, the femoral, tibial, and patellar component options could represent hundreds or thousands of different options.

Figure 3:
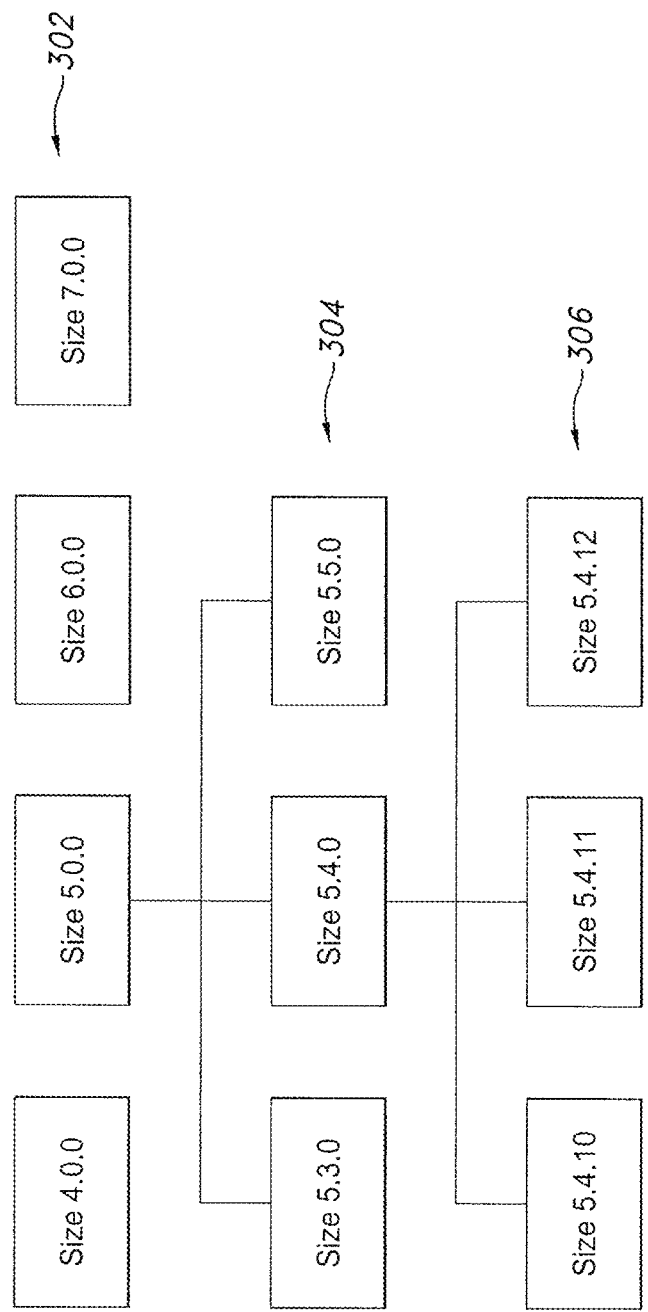
FIGS. 3 and 4 illustrate one example of a hierarchy of pre-defined implant models that may be used in conjunction with the method of FIGS. 1a and b.
Figure 4:
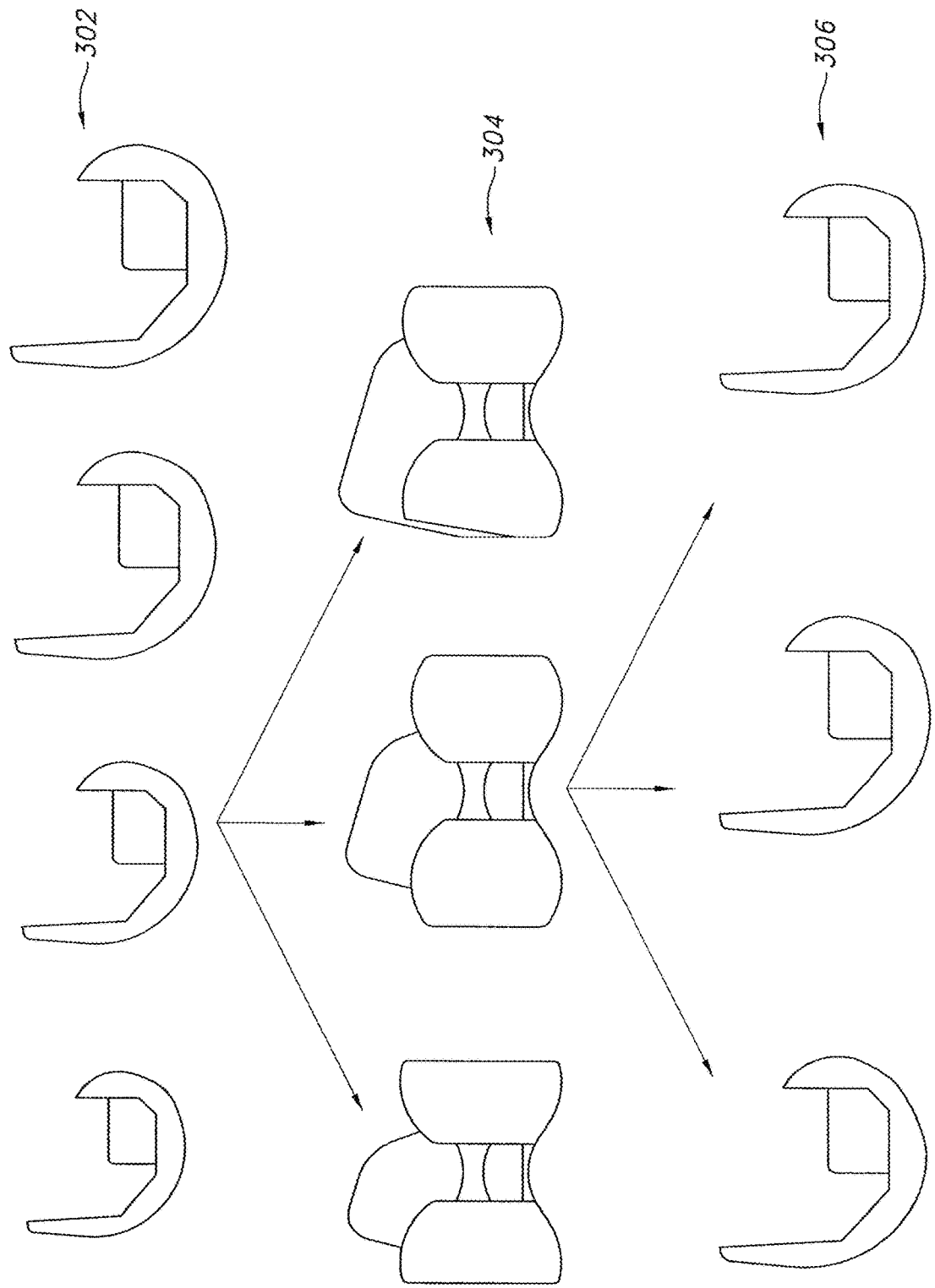

In this particular embodiment, the database of implant options is arranged in a hierarchy, which is schematically represented in FIGS. 3 and 4. Those of skill in the art will appreciate that the hierarchy shown is only one non-limiting example of how a database or other collection of implant options may be arranged, and that numerous other variants of hierarchies are possible. In still other embodiments, the implant options may not be arranged in any particular hierarchy.

In the hierarchy of FIGS. 3 and 4, the implant options are arranged at a top level 302 by general size groups, with each general size group including several sub-groups at level 304 reflecting different anatomic size options, each of which in turn include several sub-groups at level 306 reflecting different biomechanic size options. Although only a portion of the hierarchy is specifically shown in FIGS. 3 and 4, it should be understood that, in this example, the four general size options each include three anatomic size options, with each anatomic size option including three biomechanic size options (thirty-six possible combinations of general, anatomic and biomechanic size options, with nine options of anatomic and biomechanic size combinations per general size option). Other hierarchies may include more or less levels of options, with more or less options at each level. For instance, in some embodiments, there may be multiple levels of anatomic size options and multiple levels of biomechanic size options, which, in some instances, may be desirable to increase processing efficiency of the optimization algorithms discussed further below.

In the hierarchy of FIGS. 3 and 4, the general size group options may be similar to the different size options typically available for an implant (e.g. size 4, 5, 6, 7 . . . ), with smaller sizes being generally suitable for patients with smaller anatomy and larger sizes being generally suitable for patients with larger anatomy. As one non-limiting example in the context of a femoral implant, general size group option 4 may be generally appropriate for patients with femurs of a relatively small anterior-posterior dimension whereas general size group option 7 may be generally appropriate for patients with femurs of a relatively large anterior-posterior dimension.

In the hierarchy of FIGS. 3 and 4, the anatomic fit size options of level 304 may reflect different size options relating to geometries and other features of the implant that interact with the patient's anatomy. Such features include, without limitation, coverage geometry (e.g. the outer peripheral geometry of the implant and other aspects of the implant design relating to coverage of resected surfaces on the patient's anatomy), interface geometry (e.g. peg geometry and other aspects relating to how the implant interfaces with the resected surfaces), and resection geometry (e.g. reflecting possible internal geometries of the implant for interfacing with different resection geometries, such as amount of bone removed, orientation of resections relative to one another, etc.)). FIG. 4 schematically illustrates how one such feature may vary among the anatomic fit size options 304—anterior flange dimension. As shown in FIG. 4, the anatomic fit option on the left side has a relatively narrow anterior flange, whereas the anatomic fit option on the right side has a relatively wide anterior flange. Those of skill in the art will appreciate that FIG. 4 represents a simplistic, schematic representation of possible anatomic fit size options 304, and that other sets of anatomic fit size options may include many more options, and that various features of those options could vary from option to option, not just a single feature such as anterior flange dimension. Furthermore, as mentioned above, the anatomic fit options may be arranged in multiple levels, not just a single level as shown in FIGS. 3 and 4. For instance, a hierarchy may include one level reflecting options for different anterior flange dimensions, another level reflecting options for different widths of a distal, bone facing surface, and so on.

In the hierarchy of FIGS. 3 and 4, the biomechanic fit size options at level 306 may reflect different size options relating to geometries and other features of the implant that affect the biomechanic performance of the implant. Non-limiting examples of such implant geometries may include articular surface geometries. For instance, for some femoral components, the different biomechanic size options may reflect variations in shape, position, orientation, curvature or other features of medial and lateral condylar surfaces and trochlear groove surfaces of the femoral component. As one non-limiting example, FIG. 4 illustrates a set of biomechanic fit options 306 in which the left option has a relatively recessed condylar surface whereas the right option has a relatively pronounced condylar surface. As with the anatomic fit options, the biomechanic fit options may reflect changes in a variety of different features from option to option, and may be arranged in a single level (as shown in FIGS. 3 and 4) or multiple levels.

In some embodiments, the collection of implant models is not a strict hierarchy, in that, for instance, a particular biomechanic fit size option may be appropriate for use with several different anatomic fit size options, and, in at lease some embodiments, the various size options of the different levels may reflect at least somewhat independently interchangeable features. In some of these "interchangeable" embodiments, however, some combinations may not be suitable for use as an actual implant (e.g. some articular geometries may be incompatible with some coverage geometries), and thus may not be perfectly interchangeable throughout the entire collection of possible implant models.

As described further below, the three level hierarchy of FIGS. 3 and 4 corresponds to the three optimization sub-processes performed in the method of FIGS. 1a and b.

The method of FIGS. 1a and b may be generally divided into pre-processing steps, initial general size group optimization steps, biomechanic fit optimization steps, anatomic fit optimization steps, and approval/manufacturing steps. The following discusses specific, albeit non-limiting, examples of each of these steps in further detail. For purposes of explanation, the below description focuses on optimization of just a single implant component, whereas those of skill in the art will appreciate that the optimization process may be applied to an entire implant system (e.g. femoral, tibial and/or patella components) simultaneously, in parallel, in sequence, or in other manners.

1. Pre-Processing

The pre-processing steps of the method of FIGS. 1a and b include steps 102, 104, 106 and 108. At step 102, information concerning the particular patient for the orthopaedic procedure is received. In some instances, this received information includes data obtained by imaging the particular patient's joint (e.g. the knee joint of interest). Any suitable imaging technology may be used to obtain this data, including, without limitation, MRI, x-ray, CT, ultrasound, or combinations thereof. In other embodiments, non-image based technologies may be used to obtain data about the patient's joint.

In the particular embodiment illustrated, the information received at step 102 includes one or both of DICOM raw data as well as processed data obtained from an MRI. In this particular embodiment, this data includes sufficient information to identify and characterize in three dimensions relevant surfaces and other features of the patient's anatomy. Non-limiting examples of such surfaces and other features include articular surfaces of the femur, tibia, and patella (e.g. medial and lateral condylar surfaces on the femur and corresponding articular surfaces on the tibia, the trochlear groove on the femur and corresponding articular surfaces on the patella), non-articular surfaces of such anatomy, and other features of such anatomy (e.g. tibial tubercle, tibial eminence). In some embodiments, the MRI data may be sufficient to identify bone surfaces, cartilage surfaces, bone/cartilage interfaces, or other interfaces between different tissues and structures of the anatomy.

In this particular embodiment, the DICOM raw data and/or processed data obtained from the MRI also includes sufficient detail to distinguish and locate in three dimensions locations (e.g. points or areas) where soft tissues (e.g. ligaments and/or tendons) attach to the bony anatomy. Such attachment locations may include in embodiments related to knee arthroplasty, without limitation, attachment locations of the anterior and posterior cruciate ligaments, deep and superficial attachment locations of the medial collateral ligament, attachment locations of the lateral collateral ligament, insertion locations of the popliteal tendon/muscle, the iliotibial band insertion location, the patellar ligament attachment locations, and the quad tendon insertion location on the patella.

In some embodiments, an MRI scan protocol with a specific scan protocol parameter (e.g. the field of view (FOV), slice thickness, matrix, field strength, scan plane, scan time, bandwidth, etc.) is utilized to accurately produce detailed images of biological structures of interest (tendons, ligaments, muscles, cartilage and bones). The MRI scan may be performed with the patient lying supine, feet first with his or her leg in full extension and knee joint straight. In some embodiments, any leg movement will be restricted as much as possible, using padding and immobilization devices. The knee joint may be centered in the MRI coil, and the coil may be positioned as close to isocenter as possible.

In the particular embodiment of FIGS. 1*a* and *b*, the information received at step 102 also includes data sufficient to correlate a position and orientation of a mechanical axis of the patient's leg to the imaging data of the patient's joint of interest. This additional data may be obtained by an x-ray of the patient's full leg (including the hip and ankle joints) or in other manners, such as a full length MRI or CT.

In the particular embodiment shown, the information received at step 102 may also include other information about the patient and/or the surgeon's preferences about the orthopaedic procedure. Such additional information may include: information identifying the patient, identifying the surgeon, acceptable tolerances to the surgeon (e.g. amount of overhang/underhang permissible for implant coverage fit), relative importance of various orthopaedic responses to the surgeon (discussed further below), surgeon preferences regarding varus/valgus alignment, implant position and orientation, resections, sizing (upsize, downsize), soft and hard tissues analysis, bone strength DXA scores, hormone/blood markers levels, demographic information (including age, sex/gender, race/ethnicity), past medical history and comorbidities, smoking, allergies, hormonal status, hormone medications, genetics/family history, etc . . .

As shown in FIG. 1*a*, at step 104, an "enhanced" patient data set may also be received. Although shown as a separate step, step 104 may, in some embodiments, be part of the same step as step 102. The data received at step 104 may reflect information that is not included in the standard patient data received at step 102 but that is used in the optimization processes of FIGS. 1*a* and *b*. This enhanced data may include, without limitation, data reflecting the patient's gait, foot mechanics, patient anthropometrics, patient lifestyle (e.g. level of activity, types of common activities, etc.), physiological attributes (e.g. collagen levels in tissue as indicator of ligament strength), presence and characterization of previous injuries, co-morbidity data concerning other joint functionality or lack thereof, or other types of data about the patient. In some embodiments, this enhanced data may affect, directly or indirectly, the orthopaedic factors used as inputs to the biomechanic fit optimizer, which will be discussed in more detail below.

In some embodiments, the standard and enhanced data sets received in steps 102 and 104 may be collected using a web or other computer based interface allowing a user, such as a surgeon, doctor's assistant, or other user, to input/upload this data. Other data collection methods may also be utilized. In some embodiments, the types of data collected may change. For instance, in some embodiments, algorithms used for the biomechanic and anatomic fit optimizers may be updated such that different types of enhanced data are required for inputs to the optimizers, which, again, are discussed in further detail below. In such instances, the data collection interface, whether web based or otherwise, may be quickly and easily updated to reflect the different information needed.

Figure 5:
FIG. 5 shows imaging data, in this instance, a sagittal MRI image slice of a knee joint.

Returning to FIG. 1*a*, in step 106 the image data may be processed to create a three dimensional model (e.g. a CAD model) of the patient's joint or at least portions thereof. The three dimensional model may be created by segmenting or otherwise processing the imaging data to reconstruct the geometry and shape, or otherwise define the relevant surfaces and other morphological aspects of the patient's anatomy. FIG. 5 illustrates one non-limiting example of segmentation, in which individual image slices of MRI data are processed to identify boundaries (indicated by the dashed lines in FIG. 5) between the patient's femur and tibia and the surrounding anatomy. Such segmenting may be accomplished by manual, automated, or semi-automated processes. In some embodiments, segmentation may be facilitated by software packages available from, for instance, Able Software Corp of Lexington, Mass. (3D-doctor), Materialise of Leuven, Belgium (Mimics) or other software. In some embodiments, other techniques may be used to process imaging data, such as threshold based image processing, probabilistic atlas based, statistical shape modeling based, or other techniques. Some embodiments may at least partially utilize Matlab based processes (of MathWorks, Inc., Natick, Mass.) as part of such techniques.

In other embodiments, a model of the patient's joint may be created by identifying a set of points and/or dimensions in or from the image data rather than segmenting the joint surfaces in detail. For instance, in some embodiments, only certain key reference points and/or dimensions are necessary inputs to the optimization sub-processes described below, and, thus, only these reference points and dimensions need to be identified from the patient specific data (whether image or other types of data). In some embodiments, a model created from the image data need not be three dimensional.

Figure 6:
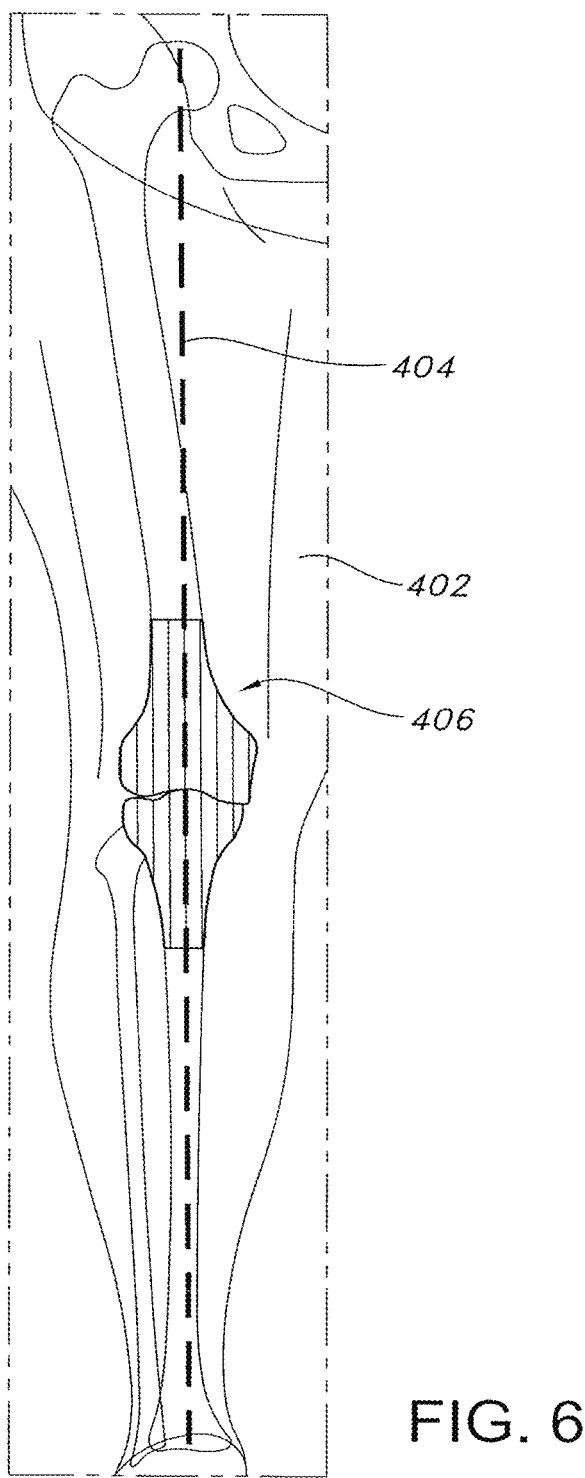
FIG. 6 shows additional imaging data, in this instance, a full length x-ray of a leg, shown with an anatomic model of a knee joint superimposed.

In some embodiments, the imaging data or other information concerning the patient may be processed to identify additional qualitative or quantitative information for incorporation into or other use with the three dimensional model, such as, but not limited to, a position and/or orientation of the mechanical axis of the patient's leg relative to the three dimensional joint model and other reference frame information (e.g. identification of particular reference points, axes or other constructs with respect to the three-dimensional anatomic model). In some embodiments, the mechanical axis of the leg and its relationship to the model of the patient's knee can be determined by overlaying a full leg x-ray of the patient on the three dimensional model. FIG. 6 shows one example of the use of a full leg length x-ray 402 to associate a mechanical axis 404 with a three dimensional anatomic model 406. In this particular embodiment, the mechanical axis 404 is defined as a line connecting the center of the femoral head to the center of the ankle joint.

Figure 7:
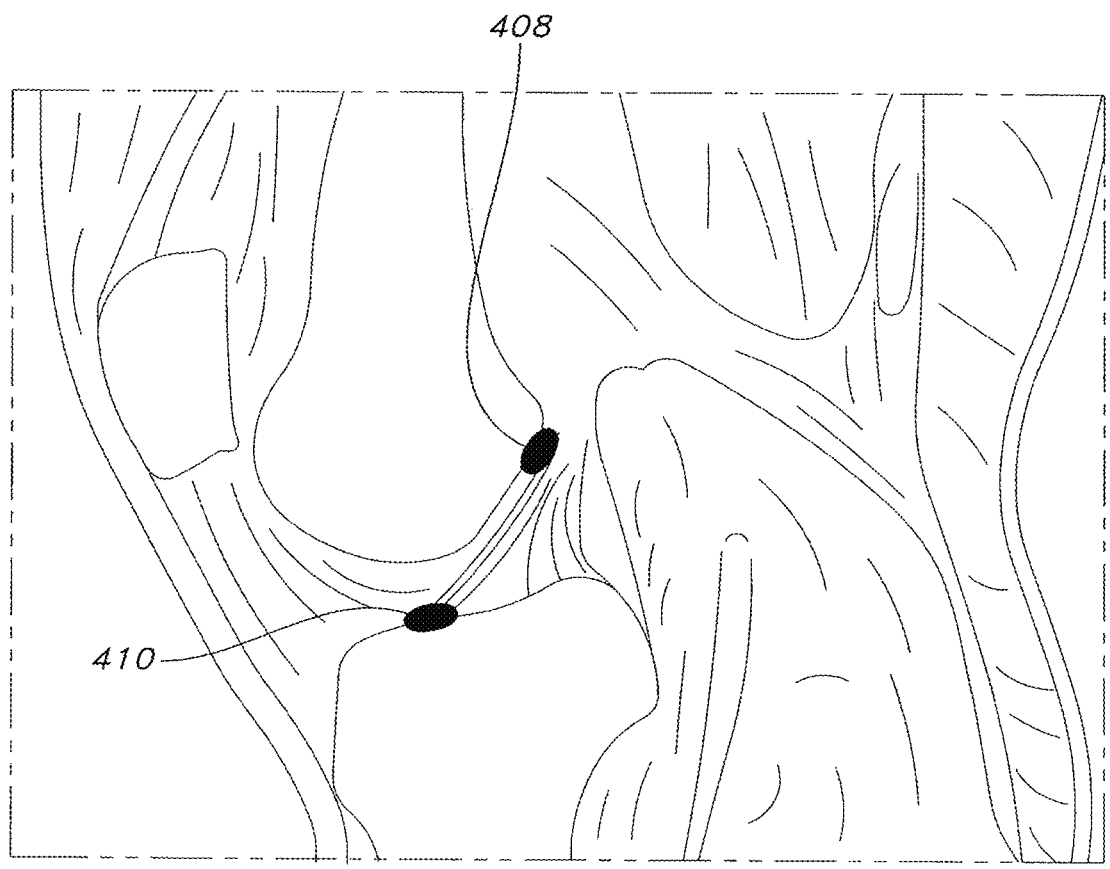
FIG. 7 shows another sagittal MRI image slice of a knee joint.

At step 108, the imaging data may also be processed to identify ligament and other soft tissue attachment locations relative to the three dimensional model. FIG. 7 illustrates use of the MRI imaging data to identify anterior cruciate ligament attachment locations 408 (the femoral attachment of the ACL on the lateral femoral condyle) and 410 (the tibial attachment of the ACL on the anterior tibial plateau). In some embodiments, step 108 may be performed simultaneously or otherwise in conjunction with other processing done to the MRI data, such as the processing performed at step 106. Moreover, as with the segmentation processes, identification of the ligament attachment locations may be done manually, semi-automatically, or using fully automated functionality.

In some embodiments, the image data and other information received concerning the particular patient may be further processed such that the three dimensional model incorporates or otherwise reflects other information, such as information relating to mechanical properties of bone (e.g. bone density), cartilage and soft tissues.

Figure 8:
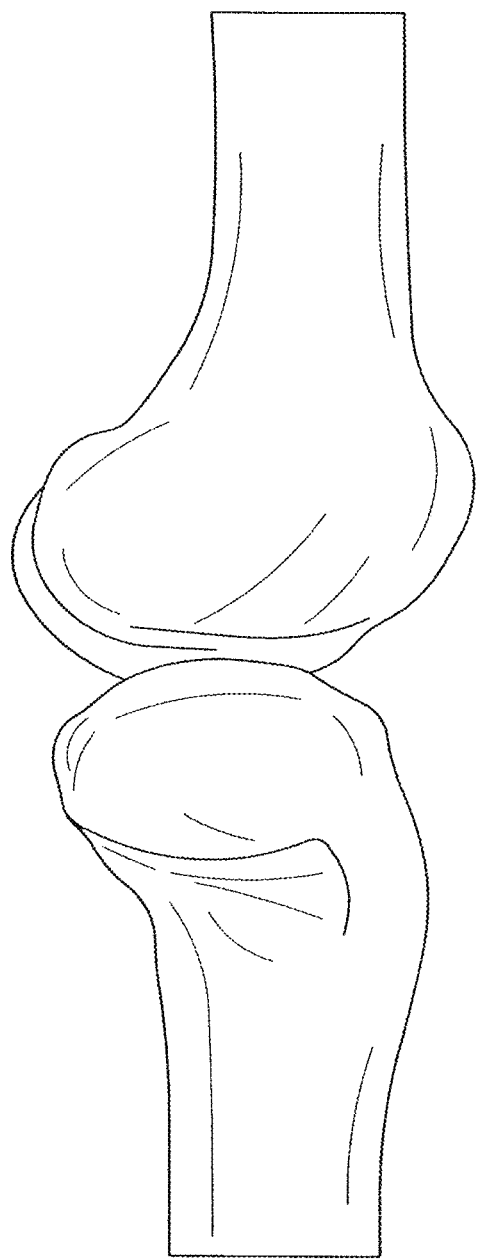
FIG. 8 shows a three dimensional anatomic model of a knee joint.

FIG. 8 illustrates an example of a three dimensional model of a particular patient's anatomy created by steps 106 and 108. Although not shown specifically in FIG. 8, the model may include visual or other indicators of a mechanical axis (from imported x-rays, raster images), bony landmarks, AP axis, epicondylar axis, ligament attachment locations and other information as discussed above.

2. Initial General Size Group Optimization

The initial general size group optimization steps of the method illustrated in FIGS. 1a and b include steps 110, 112 and 114. Steps 110-114 result in an initial selection of a general size group option (e.g. one of the general size group options 302 shown in FIGS. 3 and 4) from the possible general size groups based on (in this embodiment) relatively simple measurements of the three dimensional model of the patient's anatomy. In step 110, the three dimensional model is pre-processed in preparation for step 112. Such pre-processing may constitute a single or small number of reference measurements of the three dimensional model, such measurements similar to ones taken using traditional sizing guides to preliminarily size an implant to a patient's anatomy. For instance, in one example involving initial general size group optimization for a femur, an anterior-posterior dimension measurement of the three dimensional model, taken at a pre-defined depth and pre-defined medial-lateral position, may be determined at this step. In another example involving a tibia, a medial-lateral dimension measurement of the three dimensional model may be performed at this step.

Figure 9:
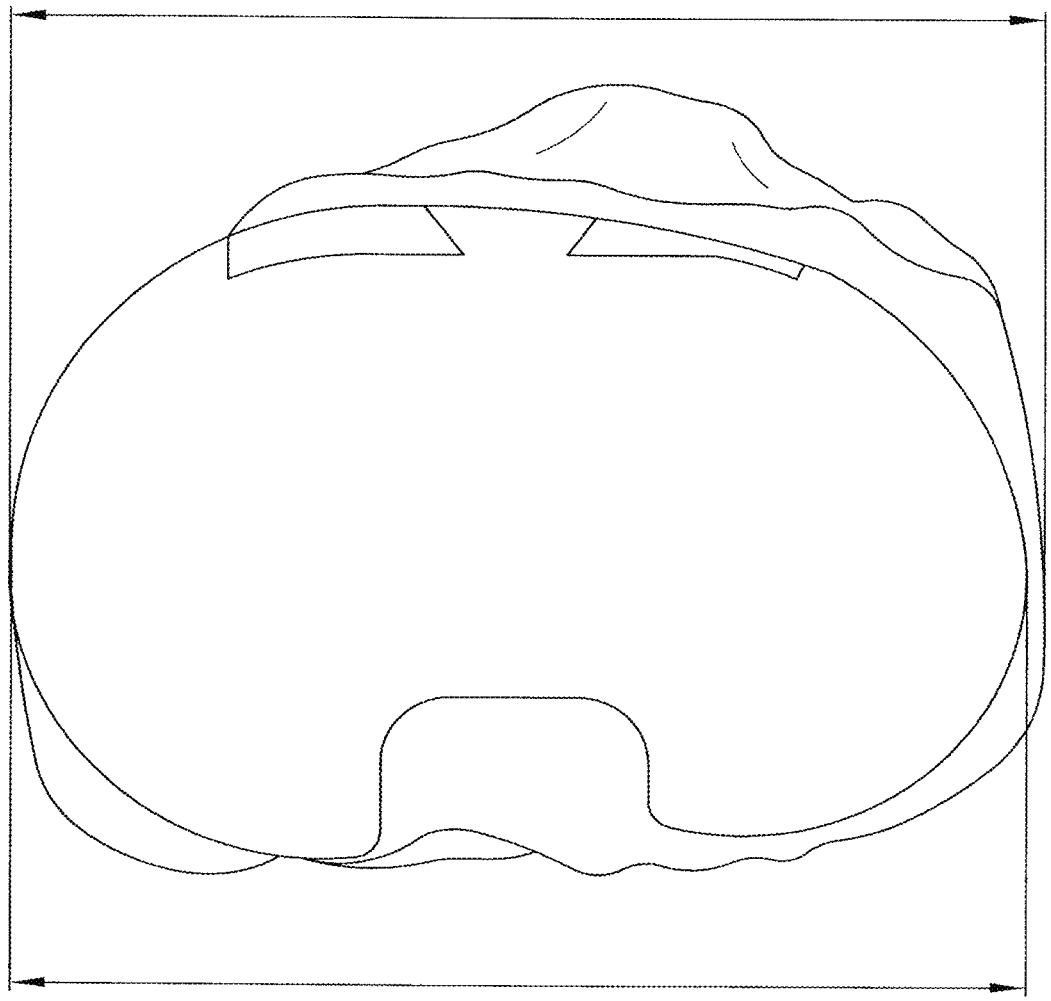
FIG. 9 schematically illustrates one non-limiting example of a general size group optimization step.

At step 112, an optimization algorithm may be used to determine the general size group option that is most appropriate based on the measurement or measurements of the three dimensional model determined at step 110. In some embodiments, such algorithm may simply select the general size group option from the possible options that has a corresponding measurement most closely matching the measurement from step 110. In some of these embodiments, the database or other collection of data reflecting the possible implant models may include data points reflecting the corresponding measurement for referencing in step 112. In other embodiments, more complex algorithms may be utilized. FIG. 9 schematically illustrates one embodiment of step 112 in which a tibial baseplate general size group option is identified that most closely fits a tibia, based on identifying the general size group option that results in the least difference between medial-lateral dimensions of the tibial implant general size group option and the anatomic model of the tibia.

Figure 10:
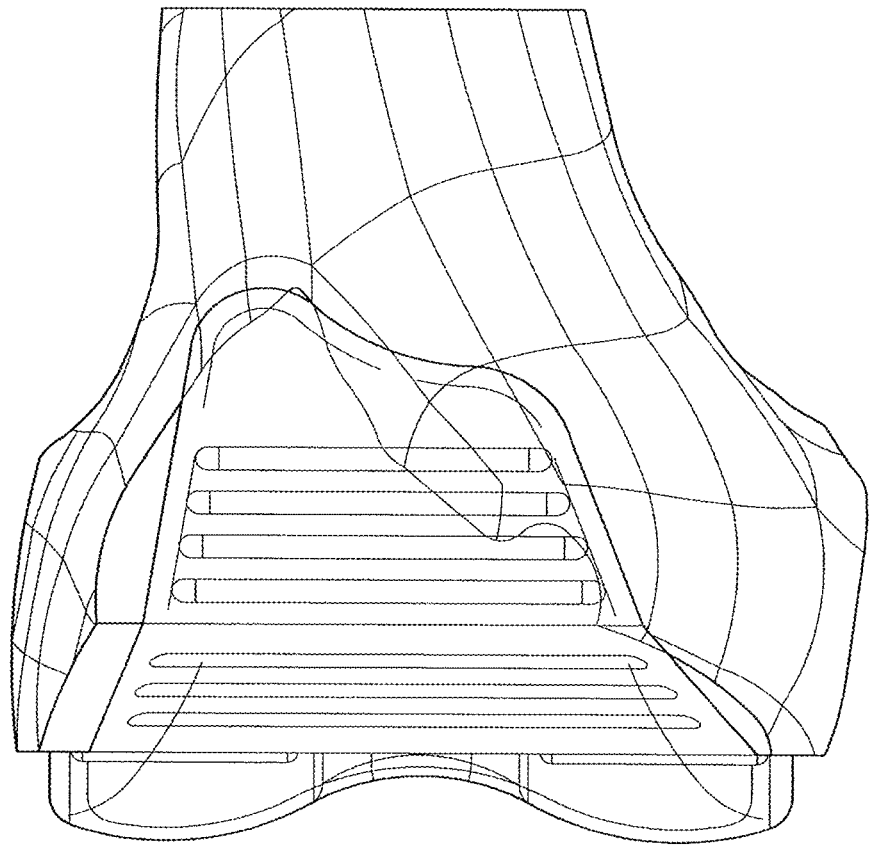
FIG. 10 schematically illustrates one non-limiting example of a verification step.

In the particular embodiment illustrated in FIGS. 1a and b, at step 114, the general size group option selected at step 112 may be verified. In some embodiments, verification may reflect manual or automated review of the general size group option selected to confirm appropriateness for the particular patient (e.g. reviewing an image of an implant reflecting the selected general size group option superimposed over the three dimensional anatomic model to ensure that it is appropriate for the particular patient). FIG. 10 illustrates one non-limiting example of an image that may be used for verification. In this example, the image may be reviewed to determine whether the general size group option (here of a femoral implant) will be satisfactory for the patient's particular anatomy (e.g. that use of the general size group option identified will not result in anterior notching of the femur). If the selected general size group option is determined to be inappropriate at step 114, the process returns to step 110 to repeat the pre-processing and/or general size group optimization steps 110 and 112 with adjusted inputs. If the selected general size group option is determined to be appropriate at step 114, the process proceeds to the biomechanic fit optimization steps discussed below. In other embodiments, verification may be delayed until a later point in the process, or may not be needed at all.

3. Biomechanic Fit Optimization

The biomechanic fit optimization steps of the method illustrated in FIGS. 1a and 1b include steps 116, 118 and 120. Steps 116-120 result in the identification of an optimal biomechanic size option for the particular patient as well as an optimal biomechanic position and orientation for implantation of the implant into the particular patient.

At step 116, data is compiled in preparation for the biomechanic fit optimization step 118. Data compiled at this step may include data related to the three dimensional model of the patient's anatomy, location and orientation of an axis, such as a mechanical axes, relative to the three dimensional model, location and orientation of soft tissue attachment locations relative to the three dimensional model, the general size group option for the implant initially identified in steps 110-114, the enhanced data received at step 104, and any surgeon preferences received at step 102. In some embodiments, the compiled data may also be processed at this point to render it suitable for use by the optimization algorithms, as discussed in further detail below.

At step 118, a biomechanic fit optimization algorithm is run. In this embodiment, the biomechanic fit optimization algorithm utilizes the patient specific data collected at step 116 (or further processed forms of that data) and at least one defined relationship between several orthopaedic factors and orthopaedic responses to determine optimal biomechanic parameters for the orthopaedic procedure. Examples of the defined relationships and orthopaedic factors and orthopaedic responses involved in those relationships are discussed in detail in U.S. provisional application Ser. No. 61/482,843, which has been incorporated by reference in its entirety into this patent application; however, a brief description of some non-limiting examples is provided below.

(a) Orthopaedic Responses

In some embodiments, the orthopaedic responses may reflect desired, measurable (quantitatively, qualitatively or categorically) performance outcomes of the orthopaedic procedure relating to the patient's gross motor skills or other outcomes. One of skill in the art will appreciate that there are numerous ways to characterize a patient's gross motor skills. Joint function, for instance, may be characterized in terms of range of motion responses, stability responses, or strength responses. At a more detailed level, these or other characteristics of joint function could be further characterized in terms of kinetic responses, kinematic responses, soft tissue balance responses (e.g. ligament tensions), etc.

In some embodiments, the orthopaedic responses do not just relate to the particular joint of interest for the orthopaedic procedure, but may also relate to other joints in the patient (e.g. one or more responses may relate to overall balance (e.g. load balance) of the patient's joint system) or overall predicted reliability/durability over time of the patient's joint system. For instance, while a particular implant and/or a particular position and orientation for implantation may provide optimal function of a particular joint when considered in isolation (e.g. optimal knee kinetics, kinematics, and ligament balance for the knee at issue), that particular implant, position and orientation may have deleterious effects on the contralateral joint or systems of joints (e.g. may negatively change the kinetics, kinematics, and/or ligament balance of the other knee, and may cause excessive wear or other damage to that knee).

The number of orthopaedic responses for use in the optimization process may vary from a few responses to hundreds or more. The method illustrated in FIGS. 1a and b may use pre-defined values for each orthopaedic response for every patient or may use values for the orthopaedic responses that vary from patient to patient (e.g. based on patient specific information, surgeon or other user preference, or on semi or fully automated functionality that selects values for the orthopaedic responses that are appropriate for the particular patient or a particular group of patients). For instance, in one example, patient specific information may reflect that the particular patient participates in activities that require a particular kinematic pattern for the joint, and, accordingly, an orthopaedic response or responses related to that particular kinematic pattern may be set at certain values to suit the particular activity.

In one non-limiting example relating to total knee arthroplasty, the particular orthopaedic responses that may be utilized for biomechanic optimization include medial and lateral condyle rollback at various degrees of flexion, maximum PCL, LCL, and/or MCL tension, maximum patellar load, and maximum quadriceps force.

(b) Orthopaedic Factors

In this embodiment, the orthopaedic factors reflect factors that have an impact (in some embodiments, significantly impact) on one or more of the orthopaedic responses. In the process illustrated in FIGS. 1a and b, the orthopaedic factors include orthopaedic factors derived from pre-operatively obtained patient specific data (e.g. the patient's specific anatomy, mechanical axis alignment, ligament and other soft tissue attachment locations, gait, foot mechanics, anthropometrics, lifestyle, physiological attributes, previous injuries, co-morbidity or other information collected at steps 102 and 104) as well as orthopaedic factors related to the parameters of the orthopaedic procedure to be optimized (e.g. implant general size group, implant biomechanic size, implant anatomic size, and position and orientation for implantation of the implant).

In at least some embodiments, many of these orthopaedic factors may be related to complex geometries (e.g. the three dimensional shape of the patient's anatomy, the shape of an articular surface reflected by a biomechanic size option, etc.) and complex movements (e.g. a gait pattern, etc.). As such, at least in some embodiments, the biomechanic optimization algorithms and the defined relationships used by those algorithms may be designed to utilize numerical values representing those complex factors. For instance, in one non-limiting example of an orthopaedic factor relating to geometry of a medial condylar articular surface for various biomechanic fit size options, a biomechanic size option with a relatively large medial condylar articular surface may be assigned a value of 5 for that particular factor whereas a biomechanic size option with a relatively small medial condylar articular surface may be assigned a value of 2 for that particular factor. Such assignment may be accomplished using manual, automated, or semi-automated sub-processes (and, in at least some embodiments, may be performed at one of the pre-processing steps such as step 116), and may utilize pre-defined coding, relationship tables or other functionality linking geometric structures, complex movements, and other characterizations of individuals and implants to particular numerical values for the orthopaedic factors. One of skill in the art will recognize that similar sub-processes may be applied to assign numerical values to complex attributes associated with orthopaedic responses. As will be discussed further below, in at least some embodiments, at least some of the orthopaedic factors and/or responses may be represented as probability distributions rather than specific numbers.

One of skill in the art will also appreciate that a huge number of orthopaedic factors may be listed as potentially impacting on the orthopaedic responses for optimization, although, in at least some instances, only a small subset of those orthopaedic factors significantly or measurably impacts on the orthopaedic responses. As discussed in U.S. provisional Ser. No. 61/482,843 as well as below, some embodiments may utilize only a limited number of key orthopaedic factors that have been identified from the host of possible orthopaedic factors using statistics based screening experiments or other methodologies.

(c) Relationship Between Orthopaedic Factors and Responses

In the embodiment shown in FIGS. 1a and b, step 118 utilizes a defined relationship or relationships between the orthopaedic factors and responses to identify an optimal biomechanic size for the orthopaedic implant as well as an optimal biomechanic position and orientation for the implant. These relationships may take a variety of forms.

In one instance, the relationship between the orthopaedic factors and responses may be in the form of a series of mathematical equations, one for each orthopaedic response. FIG. 11 schematically represents such a series of equations, with $R_1$, $R_2$, $R_3$, etc. representing the orthopaedic responses and $F_1$, $F_2$, $F_3$, etc. representing the orthopaedic factors. As can be seen in FIG. 11, each equation will not necessarily include all of the orthopaedic factors, reflecting that these orthopaedic factors impact on some, but not all, of the orthopaedic responses. Furthermore, although the equations shown in FIG. 11 are linear in nature, it is to be understood that the relationships may be non-linear in nature, such as ones in which particular factors interact with one another in non-additive manners.

The equations of FIG. 11, as well as the particular orthopaedic factors included in those defined relationships, may be determined using statistical analysis and virtual modeling tools such as the ones described in U.S. provisional application Ser. No. 61/482,843. Non-limiting examples of suitable statistical analysis tools that may be used include Design-Ease® or Design-Expert® (both available from Stat-Ease, Inc. of Minneapolis, Minn.) and Minitab® (available from Minitab, Inc. of State College, Pennsylvania). Non-limiting examples of suitable virtual modeling tools that may be used include LifeMOD™ or KneeSIM (both available from LifeModeler, Inc. of San Clemente, Calif.).

In the equations shown in FIG. 11, the orthopaedic responses ($R_1$, $R_2$, $R_3$, etc.) and factors ($F_1$, $F_2$, $F_3$, etc.) may be associated with specific numerical values, although, in at least some embodiments, at least some may be represented as a probability distribution (such as a bell curve) or in another manner reflecting uncertainty about the actual value of the orthopaedic factor or response. As such, the equations may account for uncertainty in certain aspects of this process. For instance, in at least some embodiments, it may be difficult to identify soft tissue attachment locations with certainty, and, accordingly, uncertainty information may be used reflecting a probability distribution of where such soft tissue attachment locations are actually located based on estimated locations identified during image processing. Similarly, in at least some embodiments, rather than determining an exact optimal position and orientation for the orthopaedic implant, it may be desirable to determine optimal position and orientation in the context of potential for variability in where the implant will actually be positioned and oriented (e.g. to account for tolerances in manufacturing custom cutting guide instrumentation, variability in surgeons' surgical techniques, etc.).

In some embodiments, the relationship(s) between the orthopaedic factors and responses may be defined by a set of trained neural networks rather than a series of equations. FIG. 12 schematically illustrates a set of three trained neural networks providing relationships between the factors (inputs to the neural networks) and the responses (outputs of the neural networks) via a series of interlinked nodes. Similar statistical and modeling tools to those described above may be used to define and train the neural networks and the factors used therein. In some embodiments, tools such as NeuroSolutions 6.0, available from NeuroDimensions, Inc. of Gainesville, Fla., may further facilitate the development and training of the neural networks. In some embodiments, a database of information collected from previous orthopaedic procedures or studies may be used to train the neural networks, and, as additional data is collected over time, the neural networks may be further refined to enhance the optimization processes described herein. In some embodiments, kernel methods may be used to explore the relationship(s) between the orthopaedic factors and responses. Kernel-based learning algorithms may be used to solve complex computational problems, to detect and exploit complex patterns in the data by clustering, classifying, etc.

In some embodiments, the relationship(s) may be defined by one or more trained support vector machines. Like some neural networks, a support vector machine may be trained to recognize patterns in existing data, such as data collected from previous orthopaedic procedures or studies, and, once trained, used to predict orthopaedic responses for an orthopaedic procedure for a particular patient based on settings for certain orthopaedic factors.

As described above, in at least some embodiments, one or more defined relationships (whether mathematical equations, neural networks, or other relationships) relate several orthopaedic factors to several orthopaedic responses. At the outset of step 118, values of the desired orthopaedic responses and certain orthopaedic factors (e.g. orthopaedic factors relating to the supplied patient specific information, orthopaedic factors relating to the initially identified general size group option) are known, and values for other orthopaedic factors (e.g. factors relating to a biomechanic fit size option of the orthopaedic implant and a position and orientation for implantation of the implant) are unknown. At step 118, the biomechanic fit optimizer may use the defined relationships and known values for the orthopaedic responses and factors to solve for the unknown orthopaedic factors, thereby determining optimized values for the unknown orthopaedic factors for achieving the desired orthopaedic responses.

In at least some embodiments, it may not be possible to perfectly solve all of the equations, since the orthopaedic factors may impact on the various orthopaedic responses in different ways (e.g. a biomechanic size option that provides a desired kinematic pattern for the joint may not necessarily provide a desired level of stability in the joint, and, conversely, a biomechanic size option that provides a desired level of stability in the joint may not necessarily provide a desired kinematic pattern for the joint). As such, in some embodiments, the orthopaedic responses may be associated with weighted values such that the optimization process accords greater weight to certain responses than others. These weighted values may act as desirability factors or functions quantifying the relative importance of the various orthopaedic responses.

At step 120 in FIG. 1b, the optimized values for the biomechanic fit are verified. For instance, in embodiments utilizing a database or other collection of implant models arranged in a hierarchy such as shown in FIGS. 3 and 4, it may be determined at this step whether the particular articular geometry of the biomechanic fit size option identified at step 118 is appropriate for use with the general size group option identified at step 112. Additionally, it may be determined at this step whether the particular position and orientation determined for the implant is appropriate for the general size group option identified and for the patient's particular anatomy. At step 120, an image of an implant reflecting the optimized biomechanic fit size option and position and orientation for the implant relative to the patient's anatomy may be output for verification by a user. Alternatively, key metrics concerning the optimized biomechanic fit size, position, and orientation may be output, rather than an image. As another alternative, automated or semi-automated functionality may be used for verification. In the particular embodiment shown, if the biomechanic fit parameters determined at step 118 are verified at step 120, the process proceeds to step 122. If not, the general size group or other parameters may be changed from that initially identified, and steps 116-120 repeated for the new general size group/parameters.

4. Anatomic Fit Optimization

The anatomic fit optimization steps of the method illustrated in FIGS. 1a and 1b include steps 122, 124, 126 and 128. In the particular embodiment shown, steps 122-128 result in an identification of an optimal anatomic size option for the orthopaedic implant. In other embodiments, anatomic fit optimization may also identify an optimal anatomic position and orientation for the orthopaedic implant. However, in still other embodiments, position and orientation for the implant as determined in the biomechanic fit optimization steps may be treated in the anatomic fit optimization steps as fixed and not changeable.

At step 122, the process determines which anatomic size option (e.g. from the possible anatomic size options from a database or other collection of pre-defined implant models, such as from the hierarchy of implant models shown in FIGS. 3 and 4) will best fit the anatomy of the particular patient. For instance, as shown schematically in FIG. 13 using the tibia as an example, the process may identify an outer periphery geometry 502 for an anatomic fit option of a tibial baseplate that will best fit an outer periphery 504 of a planned resection to the proximal tibia (i.e. which tibial baseplate outer periphery geometry will cover the resected surface the best without overhang). This determination may be made using the three dimensional model of the patient's anatomy, information on the different anatomic size options for the orthopaedic implant, and information on the planned position and orientation for the orthopaedic implant determined at step 118 (which, in many instances, will determine the positions and orientations for the corresponding resections to the anatomy). U.S. provisional application Ser. No. 61/509,928, which has been incorporated in its entirety into this patent application, discloses non-limiting examples of algorithms for carrying out this optimization step. As disclosed in that application and will be appreciated by those of skill in the art, these algorithms may optimize bone coverage by adjusting the position and/or orientation of the implant relative to the anatomy in addition to determining an optimal coverage geometry for the implant.

At step 124, the optimized anatomic fit (including the optimized anatomic fit size option) identified at step 122 is verified. Verification at step 124 may be performed in manners similar to the verifications described above in steps 114 and 120, may take other forms, or may, in at least some embodiments, not be necessary at all. If it is verified, the process proceeds to step 126. If not, the process returns to step 122 to re-perform the anatomic fit optimization after making any necessary adjustments.

In at least some embodiments, the biomechanic and anatomic fit optimization steps may result in a different general size group option for the orthopaedic implant being specified than what was originally determined in the initial general size group optimization steps 110-114. For instance, the biomechanic fit optimization steps may determine an optimal biomechanic size option for the particular patient that does not correspond to the general size group option originally identified in steps 110-114. Additionally, in at least some embodiments, the anatomic fit optimization steps may identify an optimal position and/or orientation for the orthopaedic implant that is different in at least some degrees of freedom from the optimal position and/or orientation for the orthopaedic implant determined by the biomechanic fit optimization steps. For instance, a position and orientation of a tibial baseplate anatomic fit size option that provides optimal coverage of a planned resection may not necessarily provide optimal biomechanic performance.

At step 126, the process determines whether the biomechanic and anatomic fit optimization steps has changed any of the optimized parameters determined in earlier steps. If so, the process proceeds to step 128 in which data concerning the change to those parameters is updated or otherwise adjusted, and the biomechanic and anatomic fit optimization steps 116-124 are re-run. At step 126, if there has not been changes to any of the optimized parameters determined in the earlier steps, the process proceeds to approval and manufacturing steps 130-136. Those of skill in the art will appreciate that steps 126 and 128 may be utilized as a feedback loop to facilitate convergence of the optimized parameters for general size group, biomechanic fit and anatomic fit to provide an overall optimized parameter set for the orthopaedic procedure.

5. Approval and Manufacturing

The approval and manufacturing steps of the process illustrated in FIGS. 1a and b include steps 130-136. In this particular embodiment, steps 130-136 result in the manufacture of an implant (in some embodiments femoral, tibial and/or patella components) and a custom cutting guide (in some embodiments custom femoral, tibial, and/or patella cutting guides) reflecting the optimized general size group, biomechanic fit, and anatomic fit determined in the earlier steps.

Figure 14:
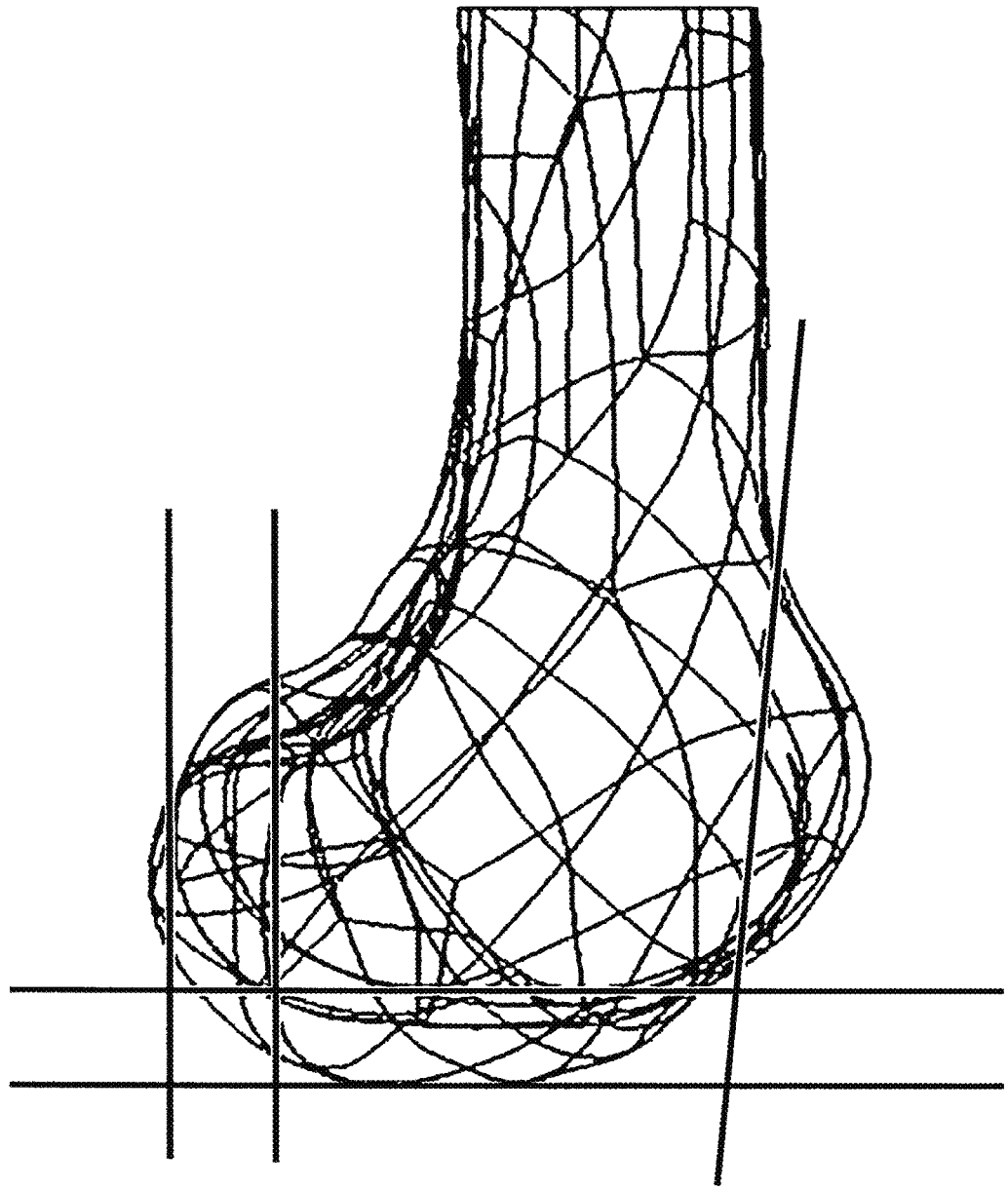
FIG. 14 illustrates an example of planned resections relative to a three dimensional model of the knee joint.

At step 130, data obtained from earlier optimization steps (e.g. data reflecting an optimal position and orientation for the implant and data reflecting an optimal implant design) may be processed to facilitate the design of a custom cutting guide or guides for the particular patient. For instance, in some embodiments, the data reflecting optimal position, orientation and implant design may be used to plan or otherwise define positions and orientations of resections to the three dimensional model of the patient's anatomy (e.g. such as the resection planes illustrated in FIG. 14). Data reflecting these planned resections, along with the three dimensional model of the patient's anatomy, may be used to customize a cutting guide to the patient's anatomy for carrying out the planned resections, such customization including the incorporation into the custom cutting guide of a surface having a shape based on the corresponding surface geometry of the patient's anatomy, as reflected in the three dimensional anatomic model.

Figure 15:
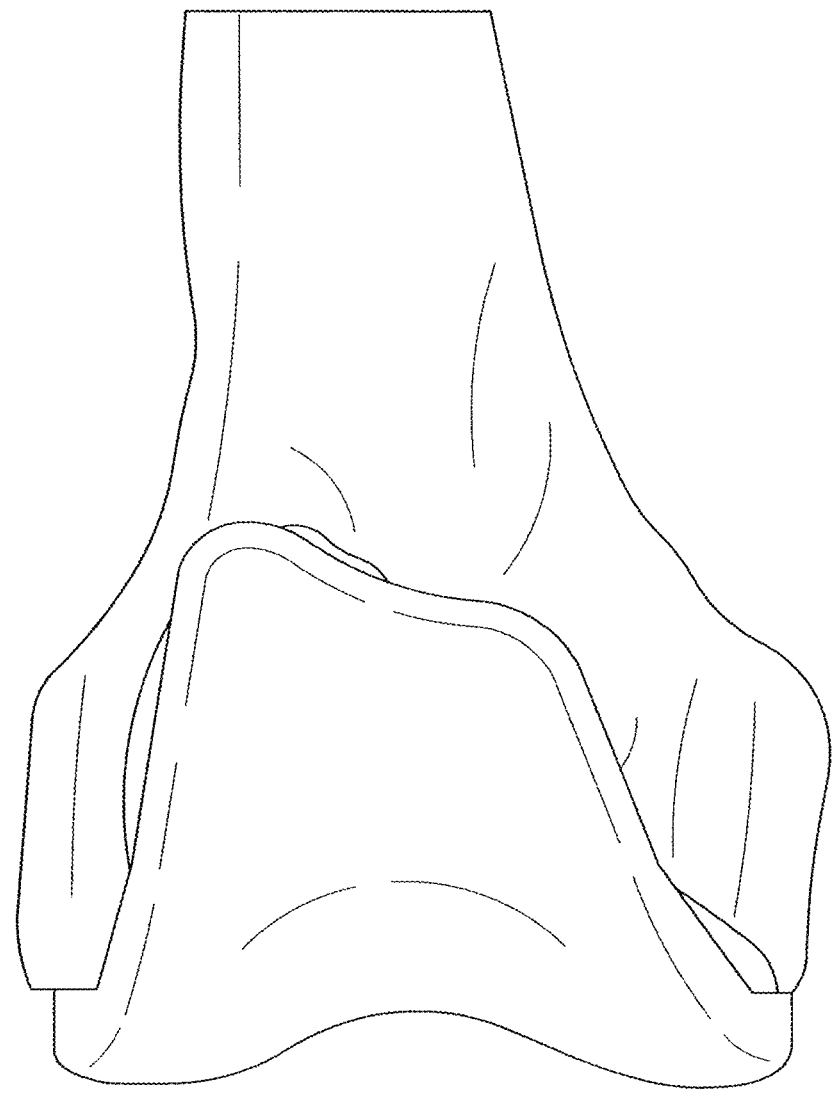
FIGS. 15 and 16 schematically illustrate one type of output (in this instance, images) used in one non-limiting example of a surgeon approval step.
Figure 16:
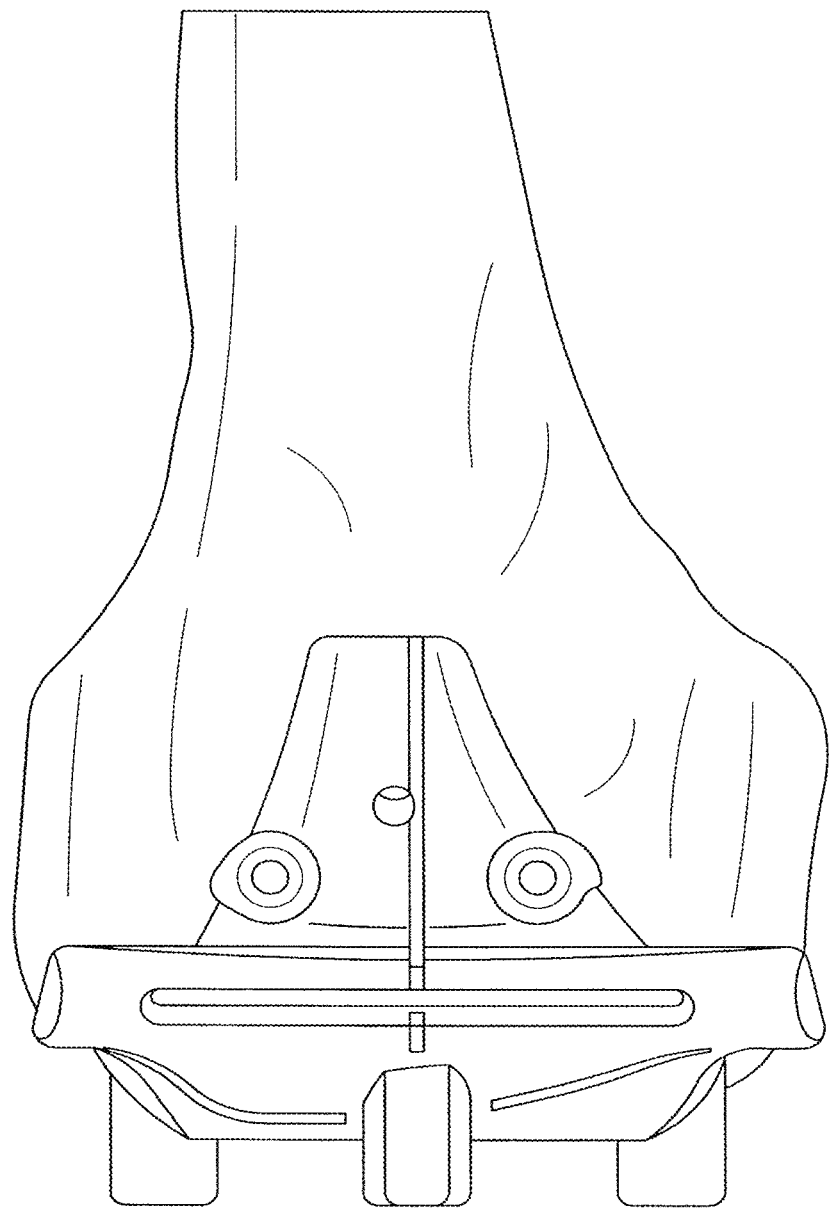

At step 132, information concerning the optimized orthopaedic procedure is output for surgeon approval. In some embodiments, the information output may be one or more images illustrating the optimized orthopaedic procedure (e.g. illustrating the proposed implant components positioned and oriented on the patient's anatomy, as shown in FIG. 15, and illustrating the proposed custom cutting guides positioned and oriented on the patient's anatomy, as shown in FIG. 16). In some embodiments, key metric data (e.g. proposed implant size, proposed varus/valgus alignment of implant, etc.) may be output instead of or in addition to the images. A variety of devices and techniques may be used to provide information about the proposed orthopaedic procedure to the surgeon, including web-based interfaces, electronic mail, or transmittal of hard copies reflecting such information. If the surgeon does not approve, the process shown in FIGS. 1a and b proceeds to step 134, where various inputs may be adjusted based on the surgeon's feedback (e.g. to utilize a different general size group, different implant alignment, etc . . . ) and the biomechanic and anatomic fit optimization steps may be re-run, although, as shown in FIG. 1b, it may not be necessary to re-run the optimizers in all instances and instead the process may simply return to step 130. If the surgeon approves, the process shown in FIGS. 1a and b proceeds to manufacturing step 136, in which the implants and/or custom cutting guides may be manufactured.

FIG. 2—Optimized Anatomic Fit

FIG. 2 schematically illustrates a non-limiting example of a method for optimizing anatomic fit of an implant to a particular patient for a total knee arthroplasty procedure. In this example, the method utilizes similar steps to those described above for the method of FIGS. 1a and b; however, this method does not optimize biomechanic fit for the particular patient, just anatomic fit. In the embodiment of FIG. 2, additional surgeon and/or user input may be required at the outset of the process. For instance, a surgeon and/or other user may need to initially specify desired positions and/or orientations for the implants (e.g. in six degrees of freedom) relative to the patient's anatomy. Such information may be specified, at least in some embodiments, by surgeon preferences or other user input based on traditional guidelines for determining implant position and/or orientation.

Computer Systems

In some embodiments, processes such as those illustrated in FIGS. 1 and 2 may be carried out, wholly or at least partially, using a computing device. The computing device may be part of or remote from the device or devices used to image the patient and the device or devices used to custom manufacture instrumentation, implants or other devices for carrying out the procedure, and may receive or access data reflecting the images obtained of the patient through any appropriate communication medium, including wireline, wireless, optical, magnetic, or solid state communication mediums. The computing device may include a processor that can execute code stored on a computer-readable medium, such as a memory. The computing device may be any device that can process data and execute code that is a set of instructions to perform actions. Examples of the computing device include a database server, a web server, desktop personal computer, a laptop personal computer, a server device, a handheld computing device, a mobile device, or combinations thereof.

In some embodiments, the processor may include a microprocessor, an application-specific integrated circuit (ASIC), a state machine, or other suitable processor. The processor may include one processor or any number of processors, and may access code stored in memory. The memory may be any non-transitory computer-readable medium capable of tangibly embodying code. The memory may include electronic, magnetic, or optical devices capable of providing processor with executable code. Examples of the memory include random access memory (RAM), read-only memory (ROM), a floppy disk, compact disc, digital video device, magnetic disk, an ASIC, a configured processor, or other storage device.

In some embodiments, the computing device may share and/or receive data with additional components through an input/output (I/O) interface. The I/O interface may include a USB port, an Ethernet port, a serial bus interface, a parallel bus interface, a wireless connection interface, or any suitable interface capable of allowing data transfers between the computing device and another component. The additional components may include components such as an information database. In other embodiments, the computing device includes the information database.

Some embodiments may include a user interface, such as a web user interface, allowing engineers, surgeons, or other users to upload data such as imaging data, documents, surgeon notes, preferences, etc. The interface could be a graphical user interface allowing a user to upload, access, visualize, annotate, and/or manipulate x-rays, MRIs, DICOM files, 3D CAD models, etc. The interface, in some embodiments, may allow the user to move the bone and implant models, and suggests different position, orientation, sizes, cutting planes, etc.

One of ordinary skill in the art will recognize that additions, deletions, substitutions or other modifications may be made to the non-limiting embodiments described above without departing from the scope or spirit of the present invention.

We claim:

1. A method of optimizing parameters relating to a joint procedure involving implantation of an orthopaedic implant into a joint of a patient, the method comprising:

receiving, by a computer processor, information concerning the patient including:
information relating to a model of the joint of the patient, wherein the information relating to the model defines a plurality of soft tissue attachment locations, and
information relating to an axis associated with the joint of the patient in relation to the model of the joint of the patient;

receiving, by the computer processor, a pre-defined relationship relating a plurality of orthopaedic responses to a plurality of orthopaedic factors, wherein (i) each orthopaedic response specifies a measurable performance outcome of the joint procedure on a gross motor skill of the patient, (ii) each orthopaedic factor is a variable that impacts one or more of the plurality of orthopaedic responses, and (iii) the pre-defined relationship is a mathematical relationship or a machine learning model;

automatically determining, by the computer processor, a suggested optimal articular surface shape geometry for the orthopaedic implant and one or more of a suggested optimal position and a suggested optimal orientation for the orthopaedic implant relative to the joint of the patient based on the plurality of soft tissue attachment locations defined by the model, the received information relating to the axis, and the received information that defines the pre-defined relationship;

determining, by the computer processor, a suggested anatomic size option for the orthopaedic implant based on the model of the joint of the patient, wherein the suggested anatomic size option is selected from a plurality of possible anatomic size options for the orthopaedic implant in a general size group, wherein each general size group comprises a plurality of different anatomic size option groups, each of the different anatomic size option groups includes a plurality of biomechanical size option groups, each of the biomechanical size option groups includes orthopaedic implant options;

determining, by the computer processor, whether the suggested optimal articular surface shape geometry for the orthopaedic implant corresponds to the suggested anatomic size option included in the general size group; and if the suggested optimal articular surface shape geometry does correspond to the suggested anatomic size option, outputting, by the computer processor, information concerning the suggested optimal articular surface shape geometry for the orthopaedic implant and the one or more of the suggested optimal position and the suggested optimal orientation for the orthopaedic implant relative to the joint of the patient.

2. The method of claim 1, wherein receiving information relating to the model of the joint of the patient comprises receiving information relating to at least one articular surface of the joint of the patient.

3. The method of claim 1, wherein receiving information relating to the model of the joint of the patient comprises receiving information relating to a three-dimensional model of the joint of the patient.

4. The method of claim 3, wherein:
receiving the information relating to the three-dimensional model of the joint of the patient includes receiving information defining a medial condylar articular surface, a lateral condylar articular surface, and a patello-femoral articular surface; and
receiving information relating to an axis associated with the joint of the patient includes receiving information defining a mechanical axis of a leg relative to the three-dimensional model of the joint of the patient.

5. The method of claim 4, wherein receiving the information relating to the three-dimensional model of the joint of the patient includes receiving information defining one or more of a tibial articular surface and a patellar articular surface.

6. The method of claim 3, further comprising:
determining, using the information relating to the three-dimensional model of the joint of the patient and the one or more of the suggested optimal position and the suggested optimal orientation for the orthopaedic implant relative to the joint of the patient, a suggested optimal size coverage geometry for the orthopaedic implant.

7. The method of claim 6, further comprising:
manufacturing the orthopaedic implant including the suggested optimal size coverage geometry and the suggested optimal articular surface shape geometry.

8. The method of claim 1, wherein receiving information concerning the patient further comprises receiving information relating to at least one of:
a gait of the patient;
an anthropometric characterization of the patient;
a lifestyle of the patient;
a physiological attribute of the patient;
an earlier injury of the patient;
a co-morbidity condition of the patient;
a demographic characterization of the patient; and
a bone strength characterization of the patient.

9. The method of claim 1, wherein determining the suggested optimal articular surface shape geometry and the one or more of the suggested optimal position and the suggested optimal orientation comprises using uncertainty information relating to the information concerning the patient.

10. The method of claim 9, wherein using the uncertainty information comprises using a probability distribution.

11. The method of claim 9, wherein using the uncertainty information comprises using a probability distribution relating at least in part to the information relating to the plurality of soft tissue attachment locations.

12. The method of claim 1, wherein the pre-defined relationship relates at least some of the orthopaedic responses to one or more of a range of motion, a joint stability, a joint strength and a ligament balance.

13. The method of claim 1, wherein the pre-defined relationship relates at least some of the orthopaedic responses to overall balance of an orthopaedic system including a plurality of joints.

14. The method of claim 1, wherein the pre-defined relationship defines a weight for each of the orthopaedic responses, wherein at least a first weight is different from at least a second weight.

15. The method of claim 1, wherein determining the suggested optimal articular surface shape geometry comprises determining a suggested optimal medial condylar articular surface shape geometry for a femoral implant, a suggested optimal lateral condylar articular surface shape geometry for the femoral implant, and a suggested optimal trochlear groove articular surface shape geometry for the femoral implant.

16. A system for optimizing parameters relating to a joint procedure involving implantation of an orthopaedic implant into a joint of a patient, the system comprising:
a processor configured to:
receive information concerning the patient including:
information relating to a model of the joint of the patient, wherein the information relating to the model defines a plurality of soft tissue attachment locations, and
information relating to an axis associated with the joint of the patient in relation to the model of the joint of the patient,
receive a pre-defined relationship relating a plurality of orthopaedic responses to a plurality of orthopaedic factors, wherein (i) each orthopaedic response specifies a measurable performance outcome of the joint procedure on a gross motor skill of the patient, (ii) each orthopaedic factor is a variable that impacts one or more of the plurality of orthopaedic responses, and (iii) the pre-defined relationship is a mathematical relationship or a machine learning model,
automatically determine a suggested optimal articular surface shape geometry for the orthopaedic implant and one or more of a suggested optimal position and a suggested optimal orientation for the orthopaedic implant relative to the joint of the patient based on the plurality of soft tissue attachment locations defined by the model, the received information relating to the axis, and the pre-defined relationship, and
determining a suggested anatomic size option for the orthopaedic implant based on the model of the joint of the patient, wherein the suggested anatomic size option is selected from a plurality of possible anatomic size options for the orthopaedic implant in a general size group, wherein each general size group comprises a plurality of different anatomic size option groups, each of the different anatomic size option groups includes a plurality of biomechanical size option groups, each of the biomechanical size option groups includes orthopaedic implant options;
determining whether the suggested optimal articular surface shape geometry for the orthopaedic implant corresponds to the suggested anatomic size option included in the general size group; and
if the suggested optimal articular surface shape geometry does correspond to the suggested anatomic size option, output information concerning the suggested optimal articular surface shape geometry for the orthopaedic implant and the one or more of the suggested optimal position and the suggested optimal orientation for the orthopaedic implant relative to the joint of the patient.

17. The system of claim 16, wherein the information relating to the model of the joint of the patient comprises information relating to at least one articular surface of the joint of the patient.

18. The system of claim 16, wherein the information relating to the model of the joint of the patient comprises information relating to a three-dimensional model of the joint of the patient.

19. The system of claim 18, wherein:
the information relating to the three-dimensional model of the joint of the patient includes information defining a medial condylar articular surface, a lateral condylar articular surface, and a patello-femoral articular surface; and
the information relating to an axis associated with the joint of the patient includes information defining a mechanical axis of a leg relative to the three-dimensional model of the joint of the patient.

20. The system of claim 19, wherein the information relating to the three-dimensional model of the joint of the patient includes information defining one or more of a tibial articular surface and a patellar articular surface.

21. The system of claim 18, wherein the processor is further configured to determine, using the information relating to the three-dimensional model of the joint of the patient and the one or more of the suggested optimal position and the suggested optimal orientation for the orthopaedic implant relative to the joint of the patient, a suggested optimal size coverage geometry for the orthopaedic implant.

22. The system of claim 21, wherein the processor is further configured to cause the system to manufacture the orthopaedic implant including the suggested optimal size coverage geometry and the suggested optimal articular surface shape geometry.

23. The system of claim 16, wherein the processor being configured to receive information concerning the patient further comprises the processor being configured to receive information relating to at least one of:
a gait of the patient;
an anthropometric characterization of the patient;
a lifestyle of the patient;
a physiological attribute of the patient;
an earlier injury of the patient;
a co-morbidity condition of the patient;
a demographic characterization of the patient; and
a bone strength characterization of the patient.

24. The system of claim 16, wherein the processor being configured to determine the suggested optimal articular surface shape geometry and the one or more of the suggested optimal position and the suggested optimal orientation comprises the processor being configured to use uncertainty information relating to the information concerning the patient.

25. The system of claim 24, wherein the processor being configured to use the uncertainty information comprises the processor being configured to use a probability distribution.

26. The system of claim 24, wherein the processor being configured to use the uncertainty information comprises the processor being configured to use a probability distribution relating at least in part to the information relating to the plurality of soft tissue attachment locations.

27. The system of claim 16, wherein the pre-defined relationship relates at least some of the orthopaedic responses to one or more of a range of motion, a joint stability, a joint strength and a ligament balance.

28. The system of claim 16, wherein the pre-defined relationship relates at least some of the orthopaedic responses to overall balance of an orthopaedic system including a plurality of joints.

29. The system of claim 16, wherein the pre-defined relationship defines a weight for each of the orthopaedic responses, wherein at least a first weight is different from at least a second weight.

30. The system of claim 16, wherein the processor being configured to determine the suggested optimal articular surface shape geometry comprises the processor being configured to determine a suggested optimal medial condylar articular surface shape geometry for a femoral implant, a suggested optimal lateral condylar articular surface shape geometry for the femoral implant, and a suggested optimal trochlear groove articular surface shape geometry for the femoral implant.

* * * * *